US012736832B2

(12) United States Patent
Brennan et al.

(10) Patent No.: US 12,736,832 B2
(45) Date of Patent: Sep. 15, 2026

(54) OPHTHALMIC LENS WITH AN OPTICALLY NON-COAXIAL ZONE FOR MYOPIA CONTROL

(71) Applicant: Johnson & Johnson Vision Care, Inc., Jacksonville, FL (US)

(72) Inventors: Noel A. Brennan, Jacksonville, FL (US); Xu Cheng, St. Johns, FL (US); Jaclyn V. Hernandez, Jacksonville, FL (US); Michael J. Collins, Jollys Lookout (AU); Brett A. Davis, Holland Park (AU); Fan Yi, Stafford Heights (AU); Derek Dean Nankivil, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 18/368,596

(22) Filed: Sep. 15, 2023

(65) Prior Publication Data

US 2024/0004221 A1 Jan. 4, 2024

Related U.S. Application Data

(60) Continuation of application No. 17/875,752, filed on Jul. 28, 2022, now Pat. No. 11,754,859, and a (Continued)

(51) Int. Cl.
*G02C 7/04* (2006.01)
*A61F 2/14* (2006.01)
(Continued)

(52) U.S. Cl.
CPC ............ *G02C 7/049* (2013.01); *A61F 2/1451* (2015.04); *A61F 2/1618* (2013.01); *G02C 7/022* (2013.01); *G02C 2202/24* (2013.01)

(58) Field of Classification Search
CPC .......... G02C 7/04; G02C 7/044; G02C 7/045; G02C 7/021; G02C 7/048; G02C 7/028;
(Continued)

(56) References Cited

U.S. PATENT DOCUMENTS 4,575,205 A 3/1986 Rappazzo
4,932,971 A 6/1990 Kelman
(Continued)

FOREIGN PATENT DOCUMENTS

CN 201804168 U 4/2011
CN 205038415 U 2/2016
(Continued)

OTHER PUBLICATIONS

Ardaya et al., "The Effect of Add Power on Distance Vision with the Acuvue Bifocal Contact Lens", Optometry—Journal of the American Optometric Association, vol. 75, No., 3, pp. 169-174, Mar. 2004.

(Continued)

*Primary Examiner* — Marin Pichler

(57) ABSTRACT

The present disclosure relates to ophthalmic devices such as ophthalmic lenses. An ophthalmic device may comprise an ophthalmic lens for at least one of slowing, retarding or preventing myopia progression. The ophthalmic lens may comprise a center zone with a negative power for myopic vision correction; and at least one treatment zone surrounding the center zone, the at least one treatment zone having a power profile comprising an ADD power, the at least one treatment zone having a surface shape comprising a portion of a generally toroidal shape, wherein the at least one treatment zone is arranged as to form a continuous surface with the center zone.

17 Claims, 31 Drawing Sheets

Related U.S. Application Data continuation of application No. 17/195,840, filed on Mar. 9, 2021, now Pat. No. 11,789,292, which is a continuation of application No. 16/724,848, filed on Dec. 23, 2019, now Pat. No. 11,768,386, which is a division of application No. 15/876,595, filed on Jan. 22, 2018, now Pat. No. 10,901,237.

(51) Int. Cl.
*A61F 2/16* (2006.01)
*G02C 7/02* (2006.01)

(58) Field of Classification Search
CPC ........ G02C 2202/24; A61F 2/14; A61F 2/142; A61F 2/145; A61F 2/1451; A61F 2/147; A61F 2/16; A61F 2/1613; A61F 2002/1696; A61F 2230/0065
USPC ...... 351/159.1, 159.12, 159.13, 159.14, 159, 351/16, 159.2, 159.21, 15, 9.53, 159.54, 351/159.71, 159.72, 159.78, 159.79, 14, 351/159.16
See application file for complete search history.

(56) References Cited

U.S. PATENT DOCUMENTS 5,225,858 A 7/1993 Portney
5,384,606 A 1/1995 Koch et al.
5,448,312 A 9/1995 Roffman et al.
5,702,440 A 12/1997 Portney
5,805,260 A 9/1998 Roffman et al.
5,929,969 A 7/1999 Roffman
5,949,519 A 9/1999 Le Saux et al.
6,045,478 A 4/2000 Ziegler et al.
6,045,578 A 4/2000 Collins et al.
6,116,735 A 9/2000 Wada
6,120,148 A 9/2000 Fiala et al.
6,196,685 B1 3/2001 Roffman et al.
6,286,956 B1 9/2001 Oyama et al.
6,536,899 B1 3/2003 Fiala
6,662,664 B2 12/2003 Ferris
7,025,460 B2 4/2006 Smith et al.
7,506,983 B2 3/2009 To et al.
7,625,086 B2 12/2009 Wooley et al.
7,665,842 B2 2/2010 Ho et al.
7,753,521 B2 7/2010 Wooley et al.
7,832,859 B2 11/2010 Phillips
7,862,171 B2 1/2011 Varnas et al.
8,240,847 B2 8/2012 Holden et al.
8,480,229 B2 7/2013 Gerligand et al.
8,529,058 B2 9/2013 Hong et al.
8,662,664 B2 3/2014 Artal et al.
8,678,584 B2 3/2014 De Juan, Jr. et al.
8,684,520 B2 4/2014 Lindacher et al.
8,931,897 B2 1/2015 Holden et al.
8,950,859 B2 2/2015 Tung
8,998,408 B2 4/2015 Wei et al.
9,594,259 B2 3/2017 Brennan et al.
9,625,739 B2 4/2017 Brennan et al.
9,638,936 B2 5/2017 Brennan et al.
9,977,257 B2 5/2018 Wooley et al.
10,061,143 B2 8/2018 Brennan et al.
10,359,646 B2 7/2019 Brennan et al.
10,768,445 B2 9/2020 Lin et al.
10,838,236 B2 11/2020 Brennan et al.
10,901,237 B2 1/2021 Brennan et al.
11,768,386 B2 9/2023 Brennan et al.
11,822,153 B2 11/2023 Wei et al.
2001/0002859 A1 6/2001 Portney
2001/0008977 A1 7/2001 Portney
2003/0045931 A1 3/2003 Lang
2004/0169820 A1 9/2004 Dai et al.
2004/0201821 A1 10/2004 Tyson
2005/0041203 A1 2/2005 Lindacher et al.
2005/0068494 A1 3/2005 Griffin
2006/0232743 A1 10/2006 Legerton
2007/0182924 A1 8/2007 Hong et al.
2007/0239043 A1 10/2007 Patel et al.
2008/0218687 A1 9/2008 Phillips
2008/0291393 A1 11/2008 Menezes
2009/0033864 A1 2/2009 Shone et al.
2009/0051870 A1 2/2009 Lindacher et al.
2009/0066912 A1 3/2009 Miura
2009/0141235 A1 6/2009 Collins et al.
2009/0187242 A1 7/2009 Weeber et al.
2010/0036489 A1 2/2010 Lindacher et al.
2010/0057202 A1 3/2010 Bogaert
2010/0066973 A1 3/2010 Portney
2010/0073629 A1 3/2010 Menezes
2010/0097569 A1 4/2010 Weeber et al.
2010/0195044 A1 8/2010 Collins et al.
2010/0328604 A1 12/2010 Collins et al.
2011/0037944 A1 2/2011 Varnas
2011/0040376 A1 2/2011 Christie et al.
2011/0153012 A1* 6/2011 Legerton .................. G02C 7/04 351/159.23
2011/0313058 A1 12/2011 Neitz et al.
2012/0057121 A1 3/2012 Dewoolfson et al.
2012/0062836 A1 3/2012 Tse et al.
2012/0113386 A1 5/2012 Back
2012/0176582 A1 7/2012 Back et al.
2012/0194780 A1 8/2012 Back
2012/0320334 A1 12/2012 Ho et al.
2012/0327363 A1 12/2012 Wooley et al.
2013/0090730 A1 4/2013 Weeber et al.
2013/0201444 A1 8/2013 Back et al.
2013/0250235 A1 9/2013 Foulds
2013/0278888 A1 10/2013 Bakaraju et al.
2013/0293834 A1 11/2013 Wang
2014/0104563 A1* 4/2014 Bakaraju ............ G02B 27/0018 351/159.52
2014/0111763 A1 4/2014 Griffin
2014/0211147 A1 7/2014 Wei et al.
2014/0268034 A1 9/2014 Wooley et al.
2014/0375949 A1 12/2014 Buehren
2015/0316788 A1 11/2015 Holden et al.
2016/0054587 A1 2/2016 Brennan et al.
2016/0054588 A1* 2/2016 Brennan .................. G02C 7/04 623/6.11
2016/0062143 A1 3/2016 Brennan
2016/0062144 A1 3/2016 Brennan et al.
2016/0062145 A1 3/2016 Brennan et al.
2016/0377884 A1* 12/2016 Lau ........................ G02C 7/022 351/159.05
2017/0010479 A1 1/2017 Meyers et al.
2017/0102556 A1 4/2017 Lindacher et al.
2017/0115509 A1 4/2017 Brennan et al.
2017/0184875 A1 6/2017 Newman
2017/0192252 A1 7/2017 Brennan et al.
2017/0227788 A1 8/2017 Griffin et al.
2017/0276961 A1* 9/2017 Wooley .................. G02C 7/027
2017/0336653 A1 11/2017 Bakaraju
2018/0017810 A1 1/2018 Wu
2018/0329229 A1 11/2018 Brennan et al.
2019/0064543 A1 2/2019 Wooley et al.
2019/0227342 A1 7/2019 Brennan et al.
2019/0353929 A1 11/2019 Lin et al.
2020/0150455 A1 5/2020 Bakaraju et al.
2021/0018762 A1 1/2021 Zheleznyak
2021/0191156 A1 6/2021 Brennan et al.
2021/0318556 A1 10/2021 Shimojo et al.
2022/0082859 A1 3/2022 Guillot et al.
2022/0179239 A1 6/2022 Chu et al.
2022/0252901 A1 8/2022 Yoon
2022/0404639 A1 12/2022 Lam et al.
2023/0011213 A1 1/2023 Brennan et al.
2023/0221579 A1 7/2023 Curatolo et al.

(56) References Cited

U.S. PATENT DOCUMENTS

| | | | |
|---|---|---|---|
| 2024/0210729 | A1 | 6/2024 | Chen et al. |
| 2024/0210735 | A1 | 6/2024 | Chen et al. |

FOREIGN PATENT DOCUMENTS

| | | | |
|---|---|---|---|
| EP | 0745876 | A2 | 12/1996 |
| EP | 0745896 | A1 | 12/1996 |
| EP | 1395203 | A1 | 3/2004 |
| EP | 1395203 | B1 | 3/2010 |
| EP | 3112925 | A1 | 1/2017 |
| EP | 3223064 | A1 | 9/2017 |
| EP | 3514613 | A1 | 7/2019 |
| EP | 3667402 | A1 | 6/2020 |
| WO | 02/100300 | A1 | 12/2002 |
| WO | 2006/113149 | A2 | 10/2006 |
| WO | 2007/146673 | A2 | 12/2007 |
| WO | 2012/034265 | A1 | 3/2012 |
| WO | 2012/173891 | A1 | 12/2012 |
| WO | 2013/015743 | A1 | 1/2013 |

OTHER PUBLICATIONS

Cheng et al., "Accommodation and its role in myopia progression and control with soft contact lenses", Ophthalmic and Physiological Optics, vol. 39, pp. 162-1710, 2019.

Cheng et al., "Impact of a Soft Contact Lens for Controlling Myopia Progression on Accommodative Response and Convergence", Poster, 1 page, 2019.

Chinese Search Report, receive for China Application No. 201910108527.9, mailed on Dec. 22, 2020, 9 pages.

Extended European Search Report, received for European Application No. 19152740.7, mailed on Apr. 2, 2019, 10 pages.

Extended European Search Report, received for European Application No. 20155158.7, dated Apr. 24, 2020, 9 pages.

Gracia et al., "Experimental Simulation of Simultaneous Vision", Investigative Ophthalmology & Visual Science, vol. 54, No. 1, pp. 415-422, Jan. 17, 2013.

Read et al., "Human Optical Axial Length and Defocus", Investigative Ophthalmology & Visual Science, vol. 51, No. 12, pp. 6262-6269, Dec. 2010.

Search Report and Written Opinion, received for Singapore Application No. 10202012980Q, mailed on Aug. 5, 2024, 8 pages.

Singapore Search Report, received for Singapore Application No. 10201900466V, mailed on Nov. 15, 2019, 3 pages.

Wildsoet et al., "Choroidal and Scleral Mechanisms of Compensation for Spectacle Lenses in Chicks", Vision Research, vol. 35, No. 9, pp. 1175-1194, May 1995.

Wirth et al., "Development of the Contact Lens User Experience: CLUE Scales", Optometry and Vision Science, vol. 93, No. 8, pp. 801-8080, Aug. 2016.

Barten, Peter G. J., "Contrast Sensitivity of the Human Eye and its Effects on Image Quality" SPIE Optical Engineering Press, 208 pages, 1999.

Belousov, V. V., "European Symposium on Vision Correction, European EyeLife Summit", Optometry Bulletin, vol. 06, pp. 22-30, Oct. 29-30, 2010.

Chen, Minghan, "Evaluating the effects of scattering on retinal image quality", Proceedings of SPIE, vol. 11941, pp. 119410B-1-119410B-6, 2022.

Donovan et al., "Myopia Progression Rates in Urban Children Wearing Single Vision Spectacles", Optometry and Vision Science, vol. 89, No. 01, pp. 27-32, Jan. 2012.

Extended European Search Report received for European Application No. 15181569.3, mailed on Nov. 26, 2015, 08 pages.

Extended European Search Report received for European Application No. 15181626.1, mailed on Nov. 19, 2015, 07 pages.

Extended European Search Report received for European Application No. 15183013.0, mailed on Dec. 21, 2015, 07 pages.

Extended European Search Report received for European Application No. 17162102.2, mailed on Jun. 16, 2017, 09 pages.

Extended European Search Report received for European Application No. 17208227.3, mailed on Mar. 29, 2018, 06 pages.

Ghosh et al., "Axial Length Changes with Shifts of Gaze Direction in Myopes and Emmetropes", IOVS, vol. 53, No. 10, pp. 6465-6471, Sep. 2012.

Guillon et al., "Real World Through Focus Curve of a New Multifocal Contact Lens", Investigative Ophthalmology & Visual Science, vol. 57, No. 12, pp. 1481, Sep. 2016.

Holden et al., "Global Prevalence of Myopia and High Myopia and Temporal Trends from 2000 through 2050", Ophthalmology, vol. 123, No. 5, pp. 1036-1042, May 2016.

International Search Report and Written Opinion, received for PCT Application No. PCT/IB2023/062928, mailed on Apr. 25, 2024, 18 pages.

International Search Report and Written Opinion, received for PCT Application No. PCT/IB2023/062930, mailed on May 3, 2024, 16 pages.

Ji et al., "Through-focus Optical Characteristics of Monofocal and Bifocal Soft Contact Lenses Across the Peripheral Visual Field", Ophthalmic & Physiological Optics, vol. 38, pp. 326-336, 2018.

Jones-Jordan et al., "Visual Activity before and after the Onset of Juvenile Myopia", Investigative Ophthalmology & Visual Science, vol. 52, No. 3, pp. 1841-1850, Mar. 2011.

Navarro et al., "Off-axis Aberrations of a Wide-angle schematic Eye Model", J. Opt. Soc. Am. A, vol. 16, No. 8, pp. 1881-1891, Aug. 1999.

NCT03408444, "Evaluating Soft Contact Lens Prototypes for Myopia Control", Johnson & Johnson Vision Care, Inc., 10 pages, 2022.

Singapore Search report received for SG Application No. 10201506380T, mailed on Jan. 29, 2016, 06 pages.

Singapore Search report received for SG Application No. 10201506431Y, mailed on Dec. 3, 2015, 6 pages.

Singapore Search report received for SG Application No. 10201506791S, mailed on Oct. 29, 2015, 11 pages.

Smith III et al., "Eccentricity-dependent Effects of Simultaneous Competing Defocus on Emmetropization in Infant Rhesus Monkeys", Vision Research, vol. 177, pp. 32-40, 2020.

Smith III et al., "Relative Peripheral Hyperopic Defocus Alters Central Refractive Development in Infant Monkeys", Vision Research, vol. 49, No. 19, pp. 2386-2392, Sep. 2009.

Thibos et al., "Accuracy and Precision of Objective Refraction from Wavefront Aberrations", Journal of Vision, vol. 4, pp. 329-351, 2004.

Walraven et al., "Relation between Directional Sensitivity and Spectral Response Curves in Human Cone Vision", Journal of the Optical Society of America, vol. 50, No. 8, pp. 780-784, Aug. 1960.

Zhelenznyak et al., "Optical and Neural Anisotropy in Peripheral Vision", Journal of Vision, vol. 16, No. 5, pp. 1-11, 2016.

* cited by examiner

500

504

508

506

502

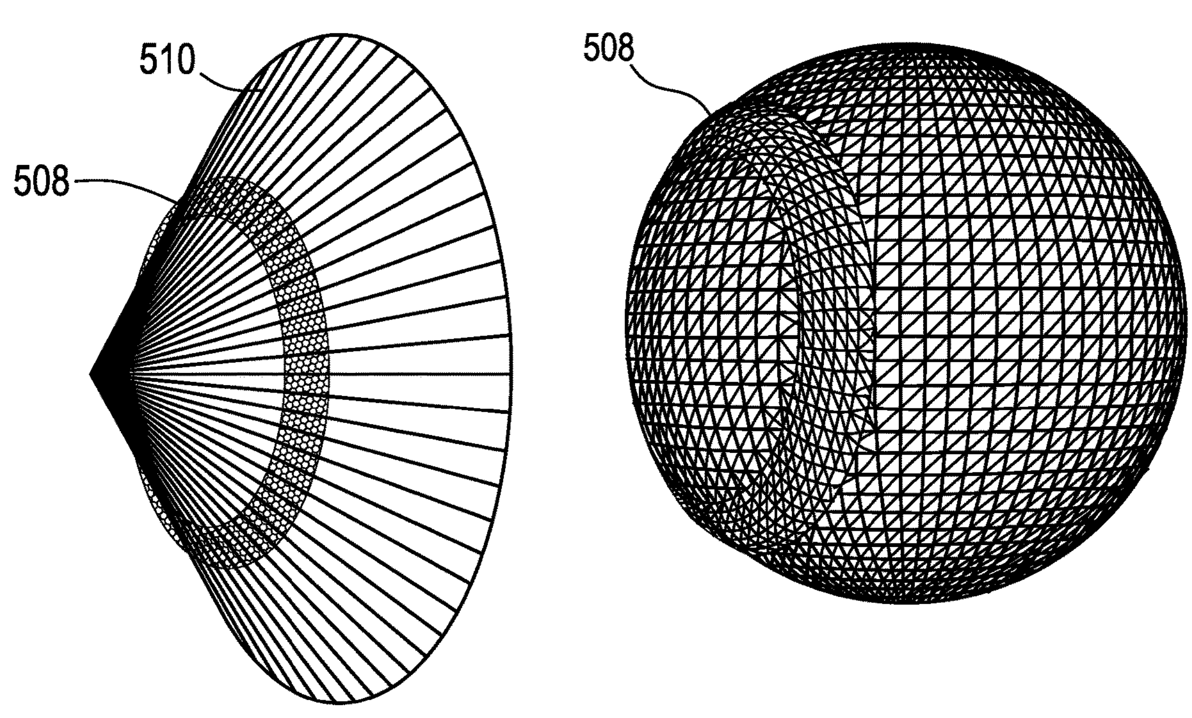
FIG. 5C
510
508
FIG. 5D
508
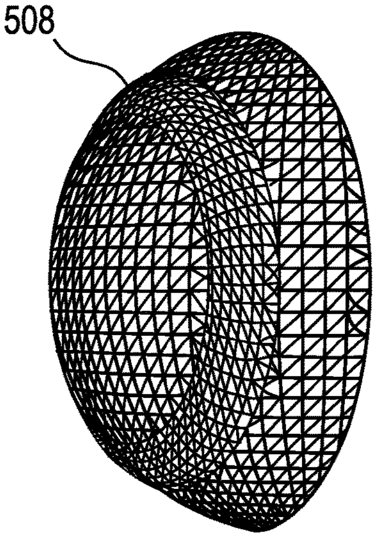
FIG. 5E
508

Point Focus

Ring Focus

Power Profile
Power (2.029)
Power (-9.474)
802
804
Center of lens
Radial Distance (mm)
Power (D)
4.00
2.00
0.00
-2.00
-4.00
-6.00
-8.00
-10.00
-0.30
0.00
0.30
0.60
0.90
1.20
1.50
1.80
2.10
2.40
2.70
3.00
3.30
3.60
3.90
4.20
4.50
4.80

Power Profile
Power (2.029)
Power (-9.474)
802
804
Center of lens
Radial Distance (mm)
Power (D)

Constructing Non-Coaxial Power Profiles
812
Radial Distance (mm)
Retinal Plane
+5D Add at Ring Focus
Principal Axis
+10D Add at
814
810
Power (2.029)
Central Coaxial Treatment Zone
818
Power (-9.474)
816
Vision Correction Zone
Non-coaxial Treatment Zone
816
Vision Correction Zone
Power = Power along Principal Axis
Power (D)
4.00
2.00
0.00
-2.00
-4.00
-6.00
-8.00
-10.00
-0.30
0.00
0.30
0.60
0.90
1.20
1.50
1.80
2.10
2.40
2.70
3.00
3.30
3.60
3.90
4.20
4.50
4.80
Radial Distance (mm)

0D wavefront 'in eye'

10D wavefront 'in eye'

Baseline
+3D Sphere
Non-coaxial +5D Design (2 Rings 20% larger area)
Non-coaxial +5D Design (2 Rings) - with TILT
Non-coaxial +5D Design (1 Ring - with center +10D Region)
Non-coaxial +5D Design (1 Ring - with center +10D Region) - with TILT
Competitor Coaxial Design ---O--- +3D Sphere
—■— Non-coaxial +2.5D Design (1 Ring with Center +5D Region) - with TILT
—△— Non-coaxial +5D Design (1 Ring with Center +10D Region) - with TILT
—✕— Non-coaxial +5D Design (1Ring) - with TILT
—✱— Non-coaxial +7D Design (2 Rings) - with TILT
—●— Competitor Coaxial Design Power
Power (0.016)
Power (0.076)
1502
1504
1506
Power (D)
12.00
10.00
8.00
6.00
4.00
2.00
0.00
-2.00
-4.00
-6.00
-0.30
0.00
0.30
0.60
0.90
1.20
1.50
1.80
2.10
2.40
2.70
3.00
3.30
3.60
3.90
4.20
4.50
4.80
Radial Distance (mm)

Power
Power (10.025)
1512
Power (0.075)
1514
1516
Power (D)
12.00
10.00
8.00
6.00
4.00
2.00
0.00
-2.00
-4.00
-6.00
-0.30
0.00
0.30
0.60
0.90
1.20
1.50
1.80
2.10
2.40
2.70
3.00
3.30
3.60
3.90
4.20
4.50
4.80
Radial Distance (mm)

Non-Inferiority Margin
Favors Control
Favors Test
Test Lens
Non-coaxial +5D Design (1 Ring with Center +10D Region) - with TILT
Non-coaxial +7D Design (2 Rings) - with TILT
Competitor Coaxial Design
-24.1
-13.2
-45.5
-60
-50
-40
-30
-20
-10
0
10
20
30
40
50
60
Difference (Test-Control)

Binocular
logMAR Visual Acuity
0.4
0.3
0.2
0.1
0.0
-0.1
-0.2
-0.3
-0.4
-0.142
-0.167
-0.219
-0.154
-0.044
-0.118
-0.005
-0.014
0.094
0.074
0.010
0.091
Standard High Contrast Bright
Standard High Contrast Dim
Standard Low Contrast Bright
Lens
ACUVUE OASYS 1-Day
Non-coaxial +5D Design (1 Ring with Center +10D Region)-with TILT
Non-coaxial +7D Design (2 Rings)-with TILT
Competitor Coaxial Design Monocular-Standard High Contrast Bright
Non-Inferiority Margin
Favors Test
Favors Control
0.065
0.037
0.051
Non-coaxial +5D Design (1 Ring with Center +10D Region) - with TILT
Non-coaxial +7D Design (2 Rings) - with TILT
Competitor Coaxial Design
Test Lens
-0.4
-0.3
-0.2
-0.1
0.0
0.1
0.2
0.3
0.4
Difference (Test-Control)

Binocular-Standard High Contrast Bright
Non-Inferiority Margin
Favors Test
Favors Control
0.077
0.052
0.065
Non-coaxial +5D Design (1 Ring with Center +10D Region) - with TILT
Non-coaxial +7D Design (2 Rings) - with TILT
Competitor Coaxial Design
Test Lens
-0.4
-0.3
-0.2
-0.1
0.0
0.1
0.2
0.3
0.4
Difference (Test-Control)

Monocular-Standard High Contrast Dim
Non-Inferiority Margin
Favors Control
Favors Test
0.100
0.053
0.115
-0.4
-0.3
-0.2
-0.1
0.0
0.1
0.2
0.3
0.4
Difference (Test-Control)
Non-coaxial +5D Design (1 Ring with Center +10D Region) - with TILT
Non-coaxial +7D Design (2 Rings) - with TILT
Competitor Coaxial Design
Test Lens Binocular-Standard High Contrast Dim
Non-Inferiority Margin
Favors Test
Favors Control
0.049
0.026
0.058
Non-coaxial +5D Design (1 Ring with Center +10D Region) - with TILT
Non-coaxial +7D Design (2 Rings) - with TILT
Competitor Coaxial Design
Test Lens
-0.4
-0.3
-0.2
-0.1
0.0
0.1
0.2
0.3
0.4
Difference (Test-Control)

Monocular-Standard Low Contrast Bright
Non-Inferiority Margin
Favors Test
Favors Control
0.125
0.084
0.129
Non-coaxial +5D Design (1 Ring with Center +10D Region) - with TILT
Non-coaxial +7D Design (2 Rings) - with TILT
Competitor Coaxial Design
Test Lens
-0.4
-0.3
-0.2
-0.1
0.0
0.1
0.2
0.3
0.4
Difference (Test-Control)

OPHTHALMIC LENS WITH AN OPTICALLY NON-COAXIAL ZONE FOR MYOPIA CONTROL

CROSS-REFERENCE TO RELATED APPLICATION

This application is a continuation of U.S. patent application Ser. No. 17/875,752 filed Jul. 28, 2022, which granted as U.S. Pat. No. 11,754,859 on Sep. 12, 2023, which is a continuation of U.S. patent application Ser. No. 17/195,840 filed Mar. 9, 2021, which granted as U.S. Pat. No. 11,789,292 on Oct. 17, 2023 which is a continuation of U.S. patent application Ser. No. 16/724,848 filed Dec. 23, 2019, which granted as U.S. Pat. No. 11,768,386 on Sep. 26, 2023, which is a divisional application of U.S. patent application Ser. No. 15/876,595, filed Jan. 22, 2018, which granted as U.S. Pat. No. 10,901,237 on Jan. 26, 2021.

BACKGROUND OF THE DISCLOSURE

1. Field of the Disclosure

The present disclosure relates to ophthalmic devices, such as wearable lenses, including contact lenses, implantable lenses, including inlays and onlays and any other type of device comprising optical components, and more particularly, to ophthalmic devices designed to slow, retard, or prevent myopia progression. The ophthalmic lenses of the present disclosure comprise at least one treatment zone with non-coaxial focus with ADD power, thereby preventing and/or slowing myopia progression.

2. Discussion of the Related Art

Ophthalmic devices, such as contact lenses, currently are utilized to correct vision defects such as myopia (nearsightedness), hyperopia (farsightedness), presbyopia and astigmatism. However, properly designed lenses may be utilized to enhance vision as well as to correct vision defects.

Common conditions which lead to reduced visual acuity are myopia and hyperopia, for which corrective lenses in the form of spectacles, or rigid or soft contact lenses, are prescribed. The conditions are generally described as the imbalance between the length of the eye and the focus of the optical elements of the eye. Myopic eyes focus in front of the retinal plane and hyperopic eyes focus behind the retinal plane. Myopia typically develops because the axial length of the eye grows to be longer than the focal length of the optical components of the eye, that is, the eye grows too long. Hyperopia typically develops because the axial length of the eye is too short compared with the focal length of the optical components of the eye, that is, the eye does not grow enough.

Myopia has a high prevalence rate in many regions of the world. Of greatest concern with this condition is its possible progression to high myopia, for example greater than five or six diopters (that is, according to sign convention, <−5.00 or −6.00 D), which dramatically affects one's ability to function without optical aids. As used herein the measure, D is the dioptric power, defined as the reciprocal of the focal distance of a lens or optical system, in meters. High myopia is also associated with an increased risk of retinal disease, cataracts, and glaucoma.

Corrective lenses are used to alter the gross focus of the eye to render a clearer image at the retinal plane, by shifting the focus from in front of the plane to correct myopia, or from behind the plane to correct hyperopia, respectively. However, the corrective approach to the conditions does not address the cause of the condition, but is merely prosthetic or only addresses the symptoms.

Most eyes do not have simple myopia or hyperopia, but have myopic astigmatism or hyperopic astigmatism. Astigmatic errors of focus cause the image of a point source of light to form as two mutually perpendicular lines at different focal distances. In the foregoing discussion, the terms myopia and hyperopia are used to include simple myopia or myopic astigmatism and hyperopia and hyperopic astigmatism respectively, or mixed astigmatism (combinations thereof).

Emmetropia describes the state of clear vision where an object at infinity is in relatively sharp focus with the crystalline lens relaxed. In normal or emmetropic adult eyes, light from both distant and close objects and passing though the central or paraxial region of the aperture or pupil is focused by the cornea and crystalline lens close to the retinal plane where the inverted image is sensed. It is observed, however, that most normal eyes exhibit positive longitudinal spherical aberration, generally with a magnitude of about +0.50 D for a 5.00 mm aperture, meaning that rays passing through the aperture or pupil at its periphery are focused +0.50 D in front of the retinal plane when the eye is focused to infinity.

The spherical aberration of the normal eye is not constant. For example, accommodation (the change in optical power of the eye derived primarily though change to the internal crystalline lens) causes the spherical aberration to change from positive to negative.

As noted, myopia typically occurs due to excessive axial growth or elongation of the eye. It is now generally accepted, primarily from animal research, that axial eye growth can be influenced by the quality and focus of the retinal image. Experiments performed on a range of different animal species, utilizing a number of different experimental paradigms, have illustrated that altering retinal image quality can lead to consistent and predictable changes in eye growth.

Furthermore, defocusing the retinal image in both chick and primate animal models, through positive lenses (myopic defocus) or negative lenses (hyperopic defocus), is known to lead to predictable (in terms of both direction and magnitude) changes in eye growth, consistent with the eyes growing to compensate for the imposed defocus. The changes in eye length associated with optical blur have been shown to be modulated by changes in both scleral growth and choroidal thickness. Blur with positive lenses, which leads to myopic blur, thickening of the choroid, and decrease in scleral growth rate, results in hyperopic refractive errors. Blur with negative lenses, which leads to hyperopic blur, thinning of the choroid, and increase in scleral growth rate, results in myopic refractive errors. These eye growth changes in response to retinal image defocus have been demonstrated to be largely mediated through local retinal mechanisms, as eye length changes still occur when the optic nerve is damaged, and imposing defocus on local retinal regions has been shown to result in altered eye growth localized to that specific retinal region.

In humans, there is both indirect and direct evidence that supports the notion that retinal image quality can influence eye growth. A variety of different ocular conditions, all of which lead to a disruption in form vision, such as ptosis, congenital cataract, corneal opacity, vitreous hemorrhage and other ocular diseases, have been found to be associated with abnormal eye growth in young humans, which suggests that relatively large alterations in retinal image quality do influence eye growth in human subjects. The influence of more subtle retinal image changes on eye growth in humans has also been hypothesized based on optical errors in the human focusing system that may provide a stimulus for eye growth and myopia development in humans.

One of the risk factors for myopia development is near work. Due to accommodative lag or negative spherical aberration associated with accommodation during such near work, the eye may experience hyperopic blur, which in turn stimulates myopia progression as discussed above. Moreover, the accommodation system is an active adaptive optical system; it constantly reacts to the vergence of the incident optics, which is impacted by optical devices as well as the working distance. With conventional single-vision optical designs for myopia correction, young eyes may show accommodative lag or have negative spherical aberration and therefore hyperopic defocus may be present. With traditional multifocal designs that incorporate coaxial ADD power in a treatment zone, as have been used for presbyopia correction and more recently repurposed for myopia control, young eyes may utilize the ADD power for near objects, yielding hyperopic defocus through the distance portion for the image of such objects. Myopia control is most effective when the user accommodates through the distance correction zone to see at near, bringing the image plane to or forward of the retina (see http://www.gslsymposium.com/getattachment/Posters/Cheng,-Xu-et-al-Impact-of-SCL-for-Myopia-Progression.pdf.aspx)

Both the single vision and multifocal cases mentioned above lead to continued myopia progression. One way to design optics to slow the rate of myopia progression is to utilize a high plus signal to the retina through use of high ADD powers. An ADD power is the difference in power between a zone of an optical device that has a special purpose, such as for correcting presbyopia or myopia control, and the myopia correction zone. For myopia control, the ADD power in the treatment zone of the optical device is more positive (more plus) or less negative compared to the power of the myopia correction zone.

U.S. Pat. No. 6,045,578 discloses that the addition of positive spherical aberration on the contact lens will reduce or control the progression of myopia. The method includes changing the spherical aberration of an ocular system by a direction and degree related to alter the growth in eye length, in other words emmetropization may be regulated by spherical aberration. In this process, the cornea of a myopic eye is fitted with a lens having increasing dioptric power away from the lens center. Paraxial light rays entering the central portion of the lens are focused on the retina of the eye, producing a clear image of an object. Marginal light rays entering the peripheral portion of the pupil are focused in a plane between the cornea and the retina, and produce positive spherical aberration of the image on the latter. This positive spherical aberration produces a physiological effect on the eye which tends to inhibit growth of the eye, thus mitigating the tendency for the myopic eye to grow longer.

Although the level of positive spherical aberration and/or plus power required to achieve an optimum slowdown in the myopia progression rate is unclear, researchers in the field have attempted to use multi-zone devices with regions of positive power of about +1.50 to a maximum of about +4.00 D ADD power in an attempt to slow the progression of myopia. For the purpose of differentiating these multi-zone designs from the current disclosure, the ADD zone in these devices produces a focus of light that coincides with the axis (principal, common, optical or geometric) of the myopia correction zone and therefore can be considered to be 'coaxial' by design. (for example, U.S. Pat. Nos. 5,929,969, 7,506,983, 7,832,859, 8,240,847)

This approach generally resulted in treatment results of less than about 50 percent. Treatment efficacy is defined as the relative change of axial length and/or spherical equivalent refraction from baseline for a test group compared to the change of axial length and/or spherical equivalent refraction of a control group over a year or a predetermined time period. There remains a need for a myopia control treatment with efficacy greater than 50 percent and closer to 100 percent. Intuitively adding treatment zones of high plus power would provide greater treatment as the ocular growth response in animals was proportional to the power of the optical stimulus as reported by Wildsoet, Vision Research 1995.

However, conventional wisdom in the field of bifocal or multifocal ophthalmic lenses assumes lenses with high plus or high ADD power may have deleterious effects on vision and contrast sensitivity as reported by Ardaya et al, Optometry 2004. Further, Smith et al (U.S. Pat. No. 7,025,460) teaches against going to powers outside the range normally found in bifocal or multifocal lenses for presbyopia. They state, "It is important to note that, while the appropriate type of refractive defocus can drive eye growth (or nongrowth) leading to myopia (or its regression) in the phenomenon of lens compensation, when the amount of refractive defocus is great, there may be such a large degradation in image quality due to the severe defocus that the optical state may change into the phenomenon of form deprivation and may induce myopia in that way." Further, they teach "that the maximum amount of relative curvature of field before substantial vision degradation occurs, which leads to form deprivation myopia, to be around the spherical equivalent of +3.50 D to +4.00 D, which represents the upper limit for negative curvature of field for effective treatment of myopia." This belief has discouraged researchers from pursuing high plus treatment zones for myopia control.

To the contrary, applicant's research shows that using a design with a central distance zone and a high ADD treatment zone having an ADD power greater than about 3.00 D reduces visual acuity loss relative to conventional low ADD type designs with no significant additional impact on contrast sensitivity. This is also supported in work by De Gracia et el., OVS 2013, although they only investigated up to 4.00 D of ADD power and did not relate the work to a potential benefit in myopia progression control. This breakthrough enables ophthalmic designs to achieve a meaningful greater than 50 percent slowdown in myopia progression without further negatively impacting visual acuity.

Further, significantly higher plus power relative to the power for providing clear distance vision is not expected to lead to reduced accommodation as may occur with a lower ADD power design where a subject might rely to some extent on that ADD power for clear vision during near work activities, as has been observed during the course of our research. This reduced accommodation may lead to hyperopic defocus as a result of rays passing through the optical zones of the device that is for providing clear distance vision (distance portion of the device or myopia correction zone). In the current disclosure, the subject must accommodate over the distance portion of the lens for near vision correction as objects imaged through the treatment zones of high ADD powers are sufficiently out of focus that they cannot be cleared with the accommodation-convergence system.

Other attempts to slow myopia progression may involve power profiles that show a gradient in some zones of the lenses. Various methodologies have been applied. Some treatment zones are progressive zones where a systematically changing coaxial focus is configured, for example, see U.S. Pat. Nos. 8,240,847, 8,662,664. Yet other designs are configured to generate a more peripheral retinal myopic defocus (for example, see U.S. Pat. Nos. 7,665,842, 8,684,520). Further, zones of some designs may be referred to as blend zones or transition zones, because they are, in effect, zones with no functional optical purpose designed to join treatment zones with correction zones. (for example, see U.S. Pat. Nos. 8,240,847, 8,684,520) None of these designs features a treatment zone comprising a portion of a generally toroidal surface to generate a ring focus as in accordance with the present disclosure.

US20170184875 contemplates "an optic feature of the lens body that directs peripheral light into the eye away from the central region of the retina when worn on the eye, wherein the optic feature further causes the peripheral light directed away from the central region of the retina to have a focal point not on the retina". It specifies that "the optic features may have the characteristic of directing the light into a peripheral region of the retina, focusing light exactly onto a peripheral region of the retina, focusing light in front of a peripheral region of the retina, focusing light behind a peripheral region of the retina, or combinations thereof." This patent does not conceive of a treatment zone comprising a portion of a generally toroidal surface to generate a ring focus as in accordance with the present disclosure.

As another example in the field, R. Griffin WO2012/173891, claims to relieve accommodative lag and accommodative stresses that lead to myopia progression through the creation of an artificial pinhole that results in increased depth of focus and depth of field. In Griffin, "the eye's accommodation is more relaxed."

With reference now to FIG. 1, the graph illustrates a device with a design that incorporates a center distance zone to correct for distance vision and a peripheral zone of variable plus power. Visual acuity was measured using a four-alternative forced choice method with progressively smaller Snellen optotypes. Increasing peripheral plus power to about +2.00 D to +3.00 D causes an increasing loss of high contrast visual acuity, as typical of multifocal type designs for presbyopes. As the peripheral power continues to increase, however, the relative effect on visual acuity surprisingly improves and plateaus, so that by above about +4.00 D to +5.00 D peripheral plus, the visual acuity loss becomes relatively constant. This is of significance for the design of myopia control lenses, since higher plus power is found (with animal models) to have a greater impact on eye growth, as reported in Wildsoet, Vision Research 1995.

However, further optimization of ADD power designs is required to optimize image quality. With reference now to FIG. 2, power profiles are illustrated having +5.00 D or +10.00 D power beyond a 2.25 mm radial location from a center of a lens. Rays passing through these high ADD power regions form sharp foci in front of the retina. However, due to continued propagation to the retina, these rays form a ring-like defocus blur on the retina.

As shown in the point spread function (PSF) cross section of FIG. 3, rays coming from the +5.00 D and +10.00 D regions form separate spikes on the retina. Thus, if one looks at a point light source through one of these +5.00 D or +10.00 D high plus lenses, his/her retina would receive a peak signal surrounded by a ring-like halo. Usually, this is not a problem when one reads letters or resolves fine details of objects because the halo is so dim that the human doesn't perceive it. Nevertheless, this is a problem if a person looks at a black/white edge, as energy from the white background can leak into the black due to the presence of the spike in PSF.

With reference now to FIG. 4, the image cross section for the +5.00 D and +10.00 D power profiles of FIG. 2 at an entrance pupil size of 6.00 mm are shown by convolving the PSF with the black/white edge in object space. A lens having 0.00 D power forms a sharp edge between the black and white (at 0.00 mm location) and thus doesn't have a ring-like structure. On the other hand, the lenses with +5.00 D and +10.00 D regions do not have a sharp edge between black and white, thereby resulting in images in which the black background is not completely black, and the white background is not completely white.

Accordingly, improvements are needed.

SUMMARY OF THE DISCLOSURE

The present disclosure relates to ophthalmic devices for at least one of slowing, retarding or preventing myopia progression that may address one or more shortcomings of the prior art.

In accordance with one aspect, the present invention is directed to an ophthalmic lens for at least one of slowing, retarding or preventing myopia progression. The ophthalmic lens comprising a center zone with a negative power for myopic vision correction, and at least one treatment zone surrounding the center zone, the at least one treatment zone having a power profile comprising a positive power relative to the center zone, the at least one treatment zone having a surface shape comprising a portion of a generally toroidal shape, wherein the at least one treatment zone is arranged as to form a continuous surface with the center zone.

In accordance with another aspect, the present invention is directed to an ophthalmic lens for at least one of slowing, retarding or preventing myopia progression. The ophthalmic lens comprising a center zone with a negative power for myopic vision correction; and at least one treatment zone surrounding the center zone, the at least one treatment zone having a power profile comprising a positive power relative to the center zone, wherein the at least one treatment zone has an annular configuration having a shared radial center point with the center zone, and wherein the at least one treatment zone generates a focal ring, with the locus of each of the infinite focal points on the ring being displaced ('non-coaxial') from the geometric axis of the center zone, and wherein the at least one treatment zone is arranged as to form a continuous surface with the center zone.

In accordance with still another aspect, the present invention is directed to an ophthalmic lens for at least one of slowing, retarding or preventing myopia progression. The ophthalmic lens comprising a center treatment zone, a myopia correction zone surrounding the center zone, wherein the myopia correction zone exhibits a negative optical power for myopic vision correction, and wherein the center zone exhibits an ADD power relative to the myopia correction zone, and at least one treatment zone surrounding the center zone and disposed radially outwardly from the myopia correction zone, the at least one treatment zone having a power profile comprising a positive power relative to the myopia correction zone, wherein the at least one treatment zone has an annular configuration having a shared radial axis with the center zone, and wherein the at least one treatment zone generates a focal ring, with the locus of each of the infinite focal points on the ring being displaced ('non-coaxial') from the geometric axis of the center zone, and wherein the at least one treatment zone is arranged as to form a continuous surface with the center zone.

In accordance with still yet another aspect, the present invention is directed to an ophthalmic lens for at least one of slowing, retarding or preventing myopia progression. The ophthalmic lens comprising a center treatment zone, a myopia correction zone surrounding the center zone, wherein the myopia correction zone exhibits a negative power for myopic vision correction, and wherein the center zone exhibits an ADD power relative to the myopia correction zone, and at least one treatment zone surrounding the center zone and disposed radially outwardly from the myopia correction zone, the at least one treatment zone having a power profile comprising a positive power, the at least one treatment zone having a surface shape comprising a portion of a generally toroidal shape, wherein the at least one treatment zone is arranged as to form a continuous surface with the center zone.

In accordance with yet another aspect, the present invention is directed to an ophthalmic lens for at least one of slowing, retarding or preventing myopia progression. The ophthalmic lens comprising a center zone with a negative power for myopic vision correction, the center zone having a principal axis orthogonal to a surface thereof and passing through a center of the ophthalmic lens, and at least one treatment zone surrounding the center zone, the at least one treatment zone having a power profile comprising a positive power relative to the center zone, the at least one treatment zone having a surface shape comprising a portion of a generally toroidal shape, wherein the at least one treatment zone is arranged as to form a continuous surface with the center zone, and wherein the at least one treatment zone has a tilt angle configured to direct an innermost ray relative to a cross section of the treatment zone to cross the principal axis at a point that is at or anterior to a retinal plane of a wearer of the ophthalmic lens.

In accordance with another aspect, the present invention is directed to an ophthalmic lens for at least one of slowing, retarding or preventing myopia progression. The ophthalmic lens comprising a center zone with a negative power and exhibiting an on-axis focal point, and at least one treatment zone surrounding the center zone, the at least one treatment zone having a power profile comprising an ADD power relative to the center zone, the at least one treatment zone exhibiting a ring focus, wherein the power profile of the treatment zone comprises a curvilinear ramp configuration.

BRIEF DESCRIPTION OF THE DRAWINGS

The foregoing and other features and advantages of the disclosure will be apparent from the following, more particular description of preferred embodiments of the disclosure, as illustrated in the accompanying drawings.

FIG. 5C illustrates a portion of a toroidal shape after the toroidal shape is cut by a conical surface.

FIG. 5D illustrates the portion of the toroidal shape disposed on an ellipsoid shape.

FIG. 5E illustrates the portion of the toroidal shape disposed on a cap, which may be a portion of the ellipsoid shape of FIG. 5D, for example.

FIG. 16A shows LSM and 95% CI of CLUE™ scores by lens type and FIG. 16B shows LSM Difference and 95% CI of CLUE™ Vision score between each of the three test lenses and the control lens.

DETAILED DESCRIPTION

Figure 1:
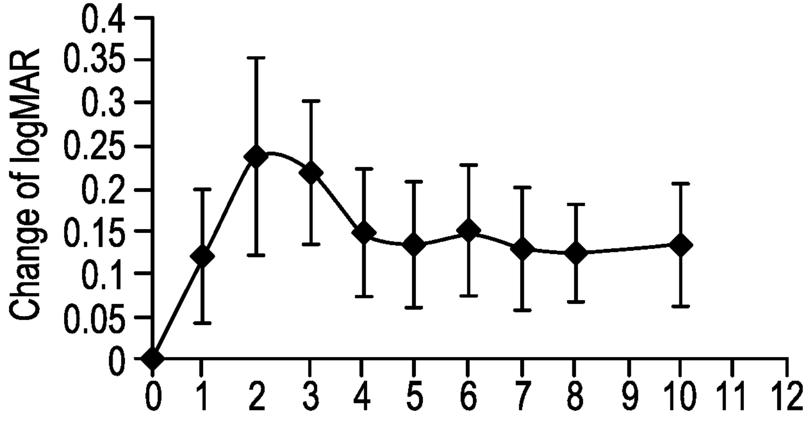
FIG. 1 illustrates a graph showing changes in visual acuity as ADD power is increased in a peripheral zone.
Figure 2:
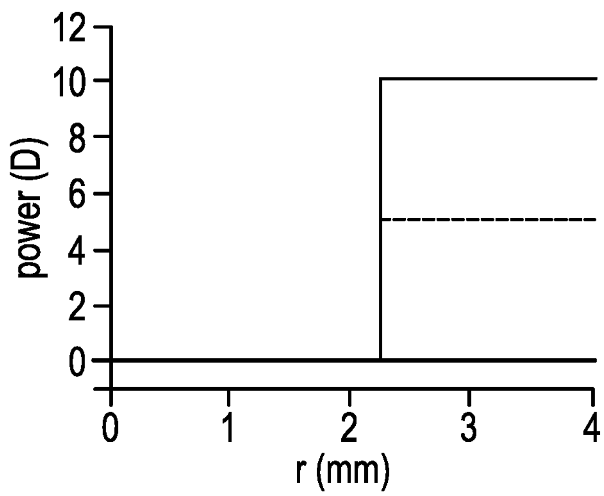
FIG. 2 illustrates power profiles of two lenses, one having a +5.00 D treatment zone and the other having a +10.00 D treatment zone.
Figure 3:
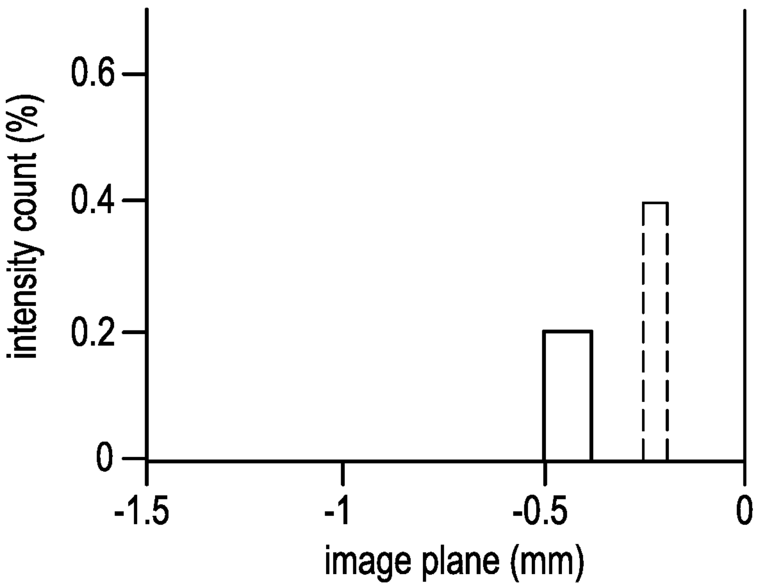
FIG. 3 illustrates a cross section of the point spread function for the power profiles of FIG. 2 at an entrance pupil size of 6.00 mm.
Figure 4:
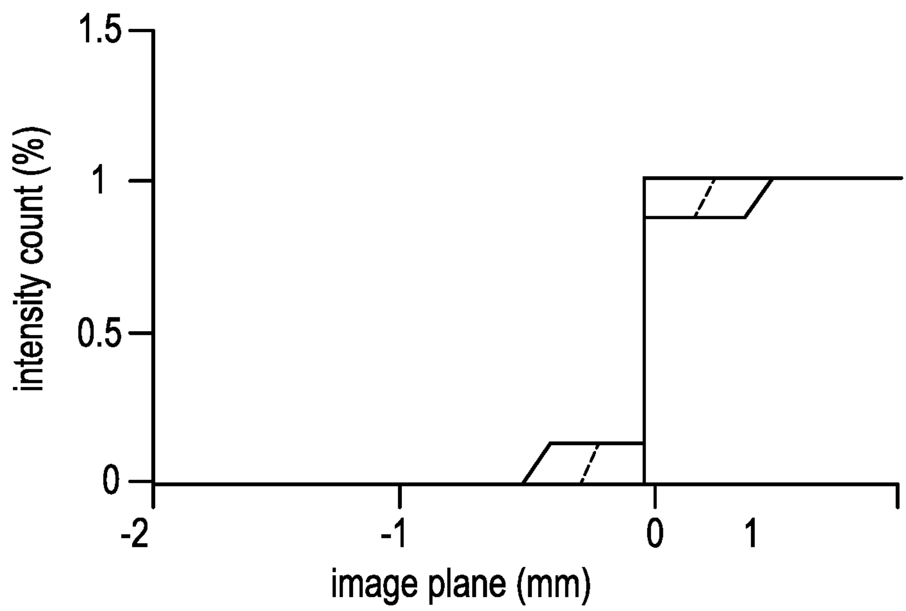
FIG. 4 illustrates a cross section of the image intensity created by the power profiles of FIG. 2 for a black and white edge.

Ophthalmic devices may include implantable devices and/or wearable devices, such as contact lenses. Conventional contact lenses comprise polymeric structures with specific shapes to correct various vision problems.

As part of a typical eye examination the Eye Care Professional may determine the contact lens prescription required to correct the patients' refractive error. This prescription may specify the refractive power, cylindrical power, and/or cylinder axis of the contact lens, which may be used in determining the design or selection of a design of a contact lens.

Optical function of a radially concentric multizone ophthalmic lens that serves at least a spherical correction purpose is most generally derived from a front and back surface. One of these surfaces may be spheroidal or ellipsoidal in nature. The other surface typically has a spheroidal or ellipsoidal cap and then one or more curved portions, each of which is the surface of a spheroidal or ellipsoidal frustum ("zone") that is symmetrically arranged so as to form a continuous surface. The zones may be radially concentric and optically coaxial about a common axis.

In an aspect, each frustum may be created by sectioning a spheroid or ellipsoid of appropriate size and shape to achieve the desired optical power, perpendicular to the principal axis of such spheroid or ellipsoid. In some cases, a transitional region (e.g., an optically dysfunctional) may be required to allow the individual zones to form a continuous surface. For myopia treatment, some of the zones will generally produce a more positive wavefront derivative than the zone or zones devoted to correct distance vision, where the wavefront derivative is taken with respect to the radial distance from the principal axis (dW/dr). Rays of light parallel to the common axis and passing through the zones will come to a principal focus for each zone, and these foci will be located on the common axis for rotationally symmetric zones. When the ophthalmic lens is used to correct vision and where one or more of the zones have principal foci of different focal length, the image formed at the retina of the eye may be blurred, or have ghosting or haloes, leading to degradation of vision.

In certain embodiments, satisfactory visual results can be achieved by preparing a zone (or replacing a designed zone of the lens) with a surface shape derived from a toroidal shape (e.g., spheroidal torus) or, in the case of replacing multiple zones, from one or more tori. As an example, the portion of the toroidal shape to be utilized may be derived from a torus (e.g., a spheroidal torus), after making a slice in the shape of the surface of a right circular cone through the surface of the spheroidal torus wherein the principal axis of the cone is coincident with the axis of rotation about which the torus is generated. The portion of the torus forming part of the lens surface is so arranged as to form a continuous surface with other zones of the lens or being joined by an optically dysfunctional, transition region to allow the individual zones to form a continuous surface. Other slices (conical or otherwise) than outlined here may also be used.

One advantage of using a torus or tori as the basis for the design of one or more zones is that the rays passing through this region of the lens would form a ring focus rather than a point focus. This dispersal of the rays can be arranged such that it results in decreased impact on vision achieved from rays passing through the corrective zone or zones of the lens. The significant benefit of such design is that visual acuity is less affected, interference with normal accommodation is minimized, and the halo effect is reduced. A larger treatment zone area and higher ADD power may be utilized as a result. The reduction of the contrast of the image is proportional to the size of the treatment zone within the pupil of the eye. The focal position of the dispersed rays is in front of the retina, and this nonetheless provides a strong myopia control effect. The ADD power, as referred to for the 'non-coaxial' foci of the present invention, refers to the positive power along the axis of the rays passing through the treatment zone, as opposed to the conventional definition of power, which is derived from the position where rays intersect a coaxial axis.

In accordance with the present disclosure, an ophthalmic lens has at least one high ADD treatment zone surrounding a center zone for treating, preventing, or slowing myopia progression, while also minimizing any halo effect.

Figures 5A, 5B:
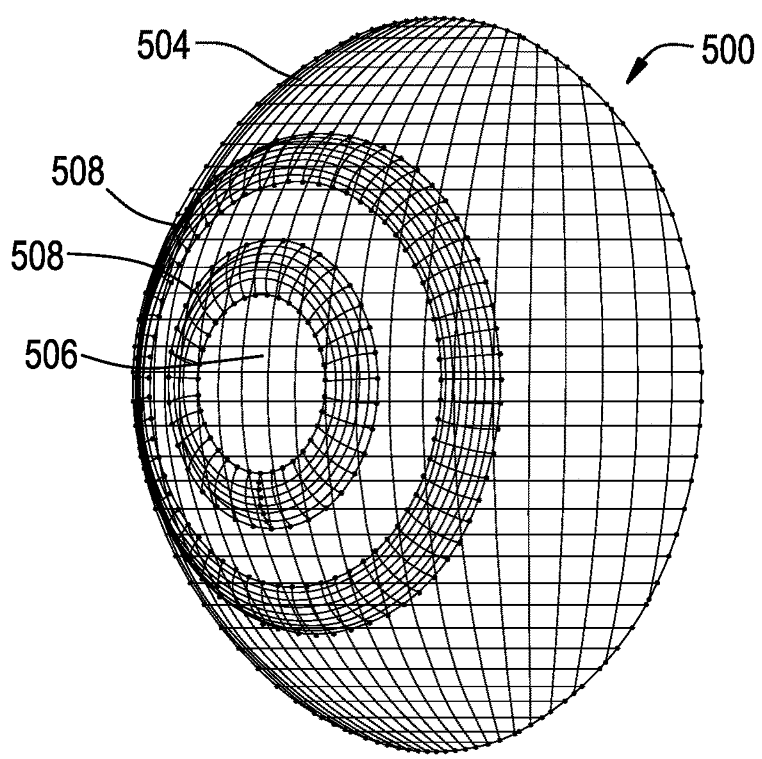
FIG. 5A illustrates a schematic representation of an example of an ophthalmic device having at least one treatment zone in accordance with the present disclosure.
FIG. 5B illustrates a perspective view of the ophthalmic device of FIG. 5A.

With reference now to FIGS. 5A-5B, there is illustrated a contact lens 500 in accordance with an embodiment of the present disclosure. The contact lens 500 comprises an optic zone 502 and an outer zone 504. The optic zone 502 comprises a first zone or center zone 506 and at least one peripheral zone or treatment zone 508. Although two treatment zones 508 are shown, a number of treatment zones may be used and positioned concentrically at various radii from a center axis. In specific embodiments, the diameter of the optic zone 502 may be selected to be 8.00 mm, the diameter of the substantially circular center zone 506 may be selected to be 4.00 mm, and the boundary diameters of an annular outer treatment zone 508 may be 5 mm and 6.5 mm as measured from the geometric center of the lens 500. As an example, the center zone 506 may be configured with a power profile to correct myopia and to provide satisfactory visual acuity. Such a power profile may comprise a negative optical power. As a further example, the at least one treatment zone 508 may be configured for treating, preventing, or slowing myopia progression. The at least one treatment zone 508 may be configured to have a surface shape that generates a focal ring, with the locus of each of the infinite focal points on the ring being displaced ('non-coaxial') from the geometric axis of the center zone 506. The optics of the treatment zone 508 may include aberrations such that rays passing through the treatment zones are not necessarily focused to a sharp ring of focus. Instead, a blurry focal ring may result. In certain aspects, the center zone 506 may include a region of ADD power, as described in FIG. 7 (zone 706).

It is important to note that FIGS. 5A-5B only illustrate an exemplary embodiment of the present disclosure. For example, in this exemplary embodiment, the outer boundary of the at least one treatment zone 508 does not necessarily coincide with the outer margin of the optic zone 502, whereas in other exemplary embodiments, they may coincide. The outer zone 504 surrounds the optic zone 502 and provides standard contact lens features, including lens positioning and centration. In accordance with one exemplary embodiment, the outer zone 504 may include one or more stabilization mechanisms to reduce lens rotation when on eye.

The various zones in FIGS. 5A-5B are illustrated as concentric annuli. The zones may comprise any suitable round or non-round shapes such as an elliptical shape. It is important to note that as the entrance pupil size of the eye varies among subpopulations, in certain exemplary embodiments, the lens design may be customized to achieve both good foveal vision correction (e.g., myopia correction) and myopia treatment efficacy based on the patient's average pupil size. Moreover, as pupil size correlates with refraction and age for pediatric patients, in certain exemplary embodiments, the lens may be further optimized towards subgroups of the pediatric subpopulation with specific age and/or refraction based upon their pupil sizes. Essentially, the lens design may be adjusted or tailored to pupil size to achieve an optimal balance between foveal vision correction and minimization of halo effect resulting from a high ADD treatment zone.

With reference to FIGS. 5C-5E, a treatment zone 508 may have a shape comprising a portion of a generally toroidal shape, wherein the at least one treatment zone 508 is arranged as to form a continuous surface with the center zone. As an example, the portion of the toroidal shape may be derived from a torus (e.g., spheroidal torus), wherein a slice through the surface of the spheroidal torus to generate the portion of the toroidal shape comprises a right circular conical surface with the principal axis of the cone 510 coincident with the axis of rotation about which the torus is generated.

Figure 5F:
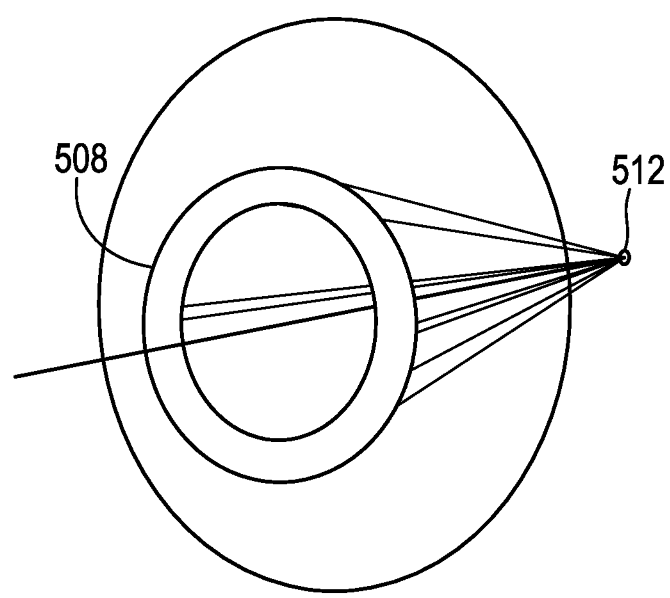
FIG. 5F illustrates a concentric treatment zone resulting in a point focus.
Figure 5G:
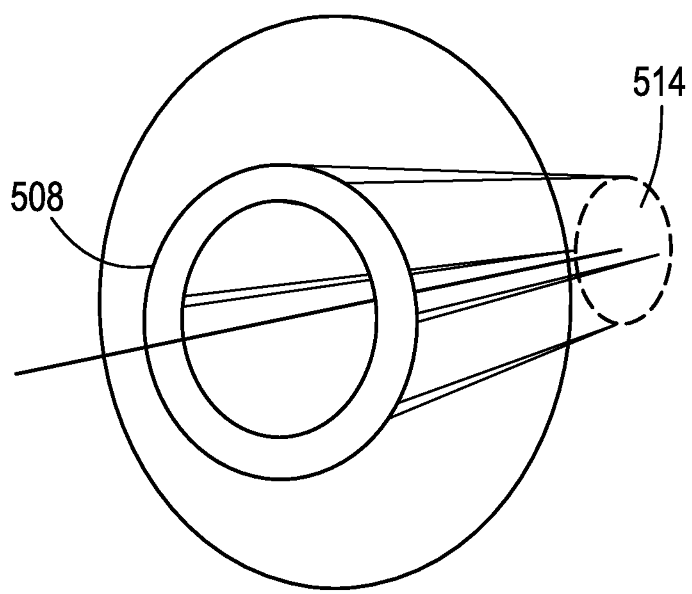
FIG. 5G illustrates a treatment zone of the present disclosure resulting in a ring focus.

With reference to FIG. 5F, the treatment zone 508 in accordance with the present disclosure may be configured to result in a point focus 512. With reference to FIG. 5G, the treatment zone 508 in accordance with the present disclosure may be configured to result in a ring focus 514. A position of the focal ring may be dependent upon the optical power of the treatment zone 508. As will be described in further detail, the focal point(s) of an annular treatment zone 508 may be a result of various surface characteristics of the treatment zone 508, including, but not limited to, a tilt of the surface of the treatment zone 508 and an optical power of the treatment zone 508.

Figure 6:
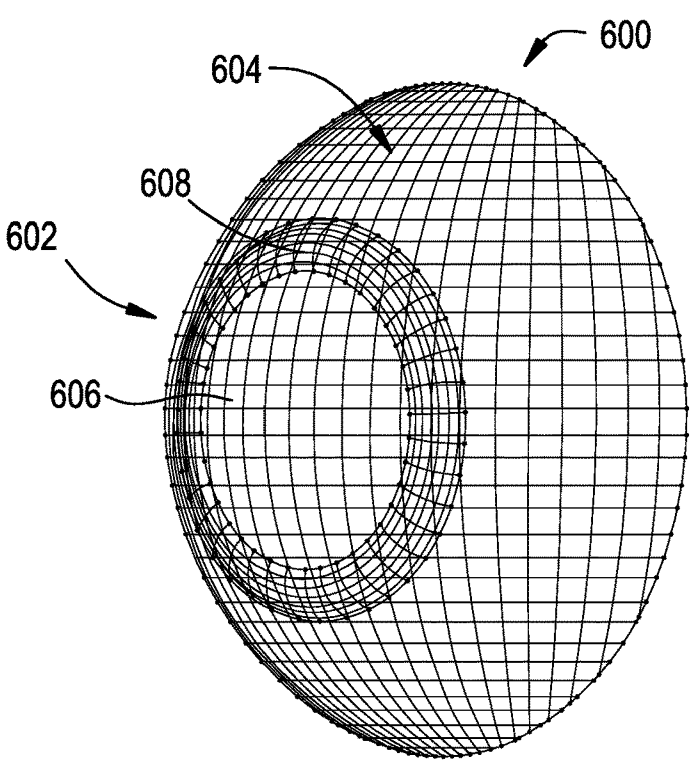
FIG. 6 illustrates an example of an ophthalmic device having a center myopia correction zone and at least one treatment zone in accordance with the present disclosure.

With reference now to FIGS. 6, there is illustrated a perspective view of a contact lens 600 in accordance with an embodiment of the present disclosure. The contact lens 600 comprises an optic zone 602 and an outer zone 604. The optic zone 602 comprises a first zone or center zone 606 and at least one treatment zone 608 or peripheral zone. In specific embodiments, the diameter of the optic zone 602 may be selected to be 8.00 mm, the diameter of the substantially circular center zone 606 may be selected to be 4.00 mm, and the boundary diameters of an annular outer treatment zone 608 may be 5 mm and 6.5 mm with reference to the geometric center of the lens 600. As an example, the center zone 606 may be configured with a power profile to correct myopia and to provide satisfactory visual acuity. Such a power profile may comprise a negative optical power. As a further example, the treatment zone 608 may be configured as a treatment zone for treating, preventing, or slowing myopia progression. The treatment zone 608 may be configured to have a surface shape that exhibits a ring focus, with the locus of each of the infinite focal points on the ring being displaced ('non-coaxial') from the geometric axis of the center zone 606. Additional treatment zones 608 may be used.

As an example, the ophthalmic lens 600 may be configured for at least one of slowing, retarding or preventing myopia progression. The ophthalmic lens may comprise the center zone 606 with a negative power for myopic vision correction and at least one peripheral zone 608 (e.g., treatment zone) surrounding the center zone 606. The at least one treatment zone 608 may have a power profile comprising an ADD power region or zone. The at least one treatment zone 608 may comprise an absolute optical power from about −10.00 D to about +15.00 D. The at least one treatment zone 608 may comprise a relative ADD power such that the optical power of the treatment zone 608 is more positive than an adjacent zone or reference zone such as the center zone 606 (e.g., a vision correction zone, a myopia correction zone, etc.). As an example, the myopia correction zone may have an optical power of −5.00 D and the treatment zone may have an optical power of −3.00 D, thus having a +2.00 D ADD power. As a further example, the myopia correction zone may have an optical power of −3.00 D and the treatment zone may have an optical power of +5.00 D, thus having a +8.00 D ADD power.

The at least one treatment zone 608 may have an annular configuration sharing a common geometric axis with the center zone 606, and wherein the at least one treatment zone 608 exhibits (that is, results in) a focal ring, with the locus of each of the infinite focal points on the ring being displaced ('non-coaxial') from the geometric axis of the center zone 606.

The at least one treatment zone 608 may have a surface shape comprising a portion of a generally toroidal shape, wherein the at least one treatment zone 608 is arranged as to form a continuous surface with the center zone. As an example, the portion of the toroidal shape to be utilized may be derived from a torus (e.g., a spheroidal torus), after making a slice in the shape of the surface of a right circular cone through the surface of the spheroidal torus wherein the principal axis of the cone is coincident with the axis of rotation about which the torus is generated.

It is important to note that FIG. 6 only illustrates an exemplary embodiment of the present disclosure. For example, in this exemplary embodiment, the outer boundary of the at least one treatment zone 608 does not necessarily coincide with the outer margin of the optic zone 602, whereas in other exemplary embodiments, they may coincide. The outer zone 604 surrounds the optic zone 602 and provides standard contact lens features, including lens positioning and centration. In accordance with one exemplary embodiment, the outer zone 604 may include one or more stabilization mechanisms to reduce lens rotation when on eye.

Figure 7:
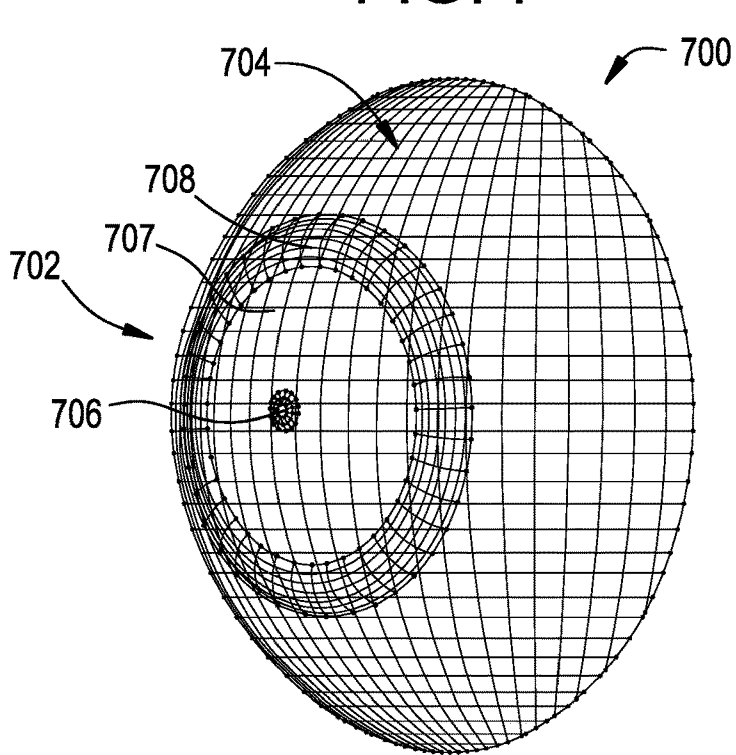
FIG. 7 illustrates an example of an ophthalmic device having a center treatment zone, a myopia correction zone, and at least one treatment zone in accordance with the present disclosure.

With reference now to FIGS. 7, there is illustrated a perspective view of a contact lens 700 in accordance with an embodiment of the present disclosure. The contact lens 700 comprises an optic zone 702 and an outer zone 704. The optic zone 702 comprises a first zone or center zone 706 and at least one peripheral treatment zone 708, and a myopia correction zone 707 disposed between the center zone 706 and the at least one peripheral treatment zone 708. In specific embodiments, the diameter of the optic zone 702 may be selected to be 8.0 mm, the diameter of the substantially circular center zone 706 may be selected to be 4.0 mm, and the boundary diameters of an annular outer treatment zone 708 may be 5 mm and 6.5 mm with reference to the geometric center of the lens 700. As an example, the center zone 706 may be configured with a power profile having an ADD power. This center zone 706 may be configured to exhibit (that is, result in) a focal point between the lens 700 and a retinal plane of a wearer to treat myopia and to provide satisfactory visual acuity. A myopia correction zone 707 may be configured to surround the center zone 706 and may be configured with a power profile to correct distance vision for myopia. Such a power profile may comprise a negative optical power. As a further example, the treatment zone 708 may be configured as a treatment zone for treating, preventing, or slowing myopia progression. The treatment zone 708 may be configured to have a surface shape the exhibits (that is, results in) a focal ring, with the locus of each of the infinite focal points on the ring being displaced ('non-coaxial') from the geometric axis of the center zone 706. Additional treatment zones 708 may be used. The at least one treatment zone 708 may have a power profile comprising an ADD power region or zone such as the center zone 706. The at least one treatment zone 708 may comprise an absolute optical power from about −10.00 D to about +15.00 D. The at least one treatment zone 708 may comprise a relative ADD power such that the optical power of the treatment zone 708 is more positive than an adjacent zone or reference zone such as the center zone 707 (e.g., a vision correction zone, a myopia correction zone, etc.). As an example, the myopia correction zone may have an optical power of −5.00 D and the treatment zone may have an optical power of −3.00 D, thus having a +2.00 D ADD power. As a further example, the myopia correction zone may have an optical power of −3.00 D and the treatment zone may have an optical power of +5.00 D, thus having a +8.00 D ADD power.

The at least one treatment zone 708 may have an annular configuration sharing a common geometric axis with the center zone 706, and wherein the at least one treatment zone 708 exhibits a focal ring, with the locus of each of the infinite focal points on the ring being displaced ('non-coaxial') from the geometric axis of the center zone 706.

The at least one treatment zone 708 may have a surface shape comprising a portion of a generally toroidal shape, wherein the at least one treatment zone 708 is arranged as to form a continuous surface with the center zone. As an example, the portion of the toroidal shape to be utilized may be derived from a torus (e.g., a spheroidal torus), after making a slice in the shape of the surface of a right circular cone through the surface of the spheroidal torus wherein the principal axis of the cone is coincident with the axis of rotation about which the torus is generated.

It is important to note that FIG. 7 only illustrates an exemplary embodiment of the present disclosure. For example, in this exemplary embodiment, the outer boundary of the at least one treatment zone 708 does not necessarily coincide with the outer margin of the optic zone 702, whereas in other exemplary embodiments, they may coincide. The outer zone 704 surrounds the optic zone 702 and provides standard contact lens features, including lens positioning and centration. In accordance with one exemplary embodiment, the outer zone 704 may include one or more stabilization mechanisms to reduce lens rotation when on eye.

Figures 8A, 8B:
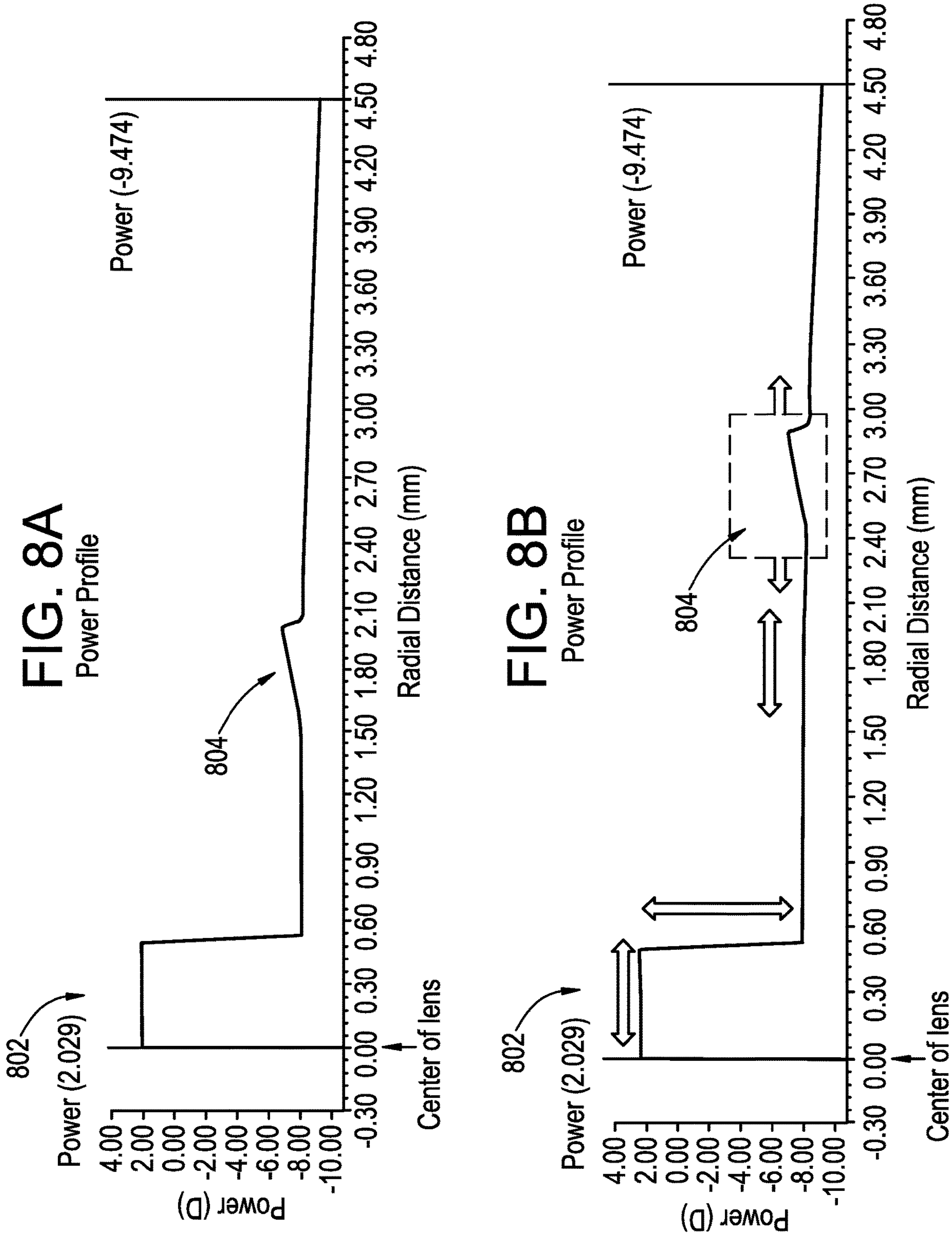
FIG. 8A illustrates a power profile of an ophthalmic device.
FIG. 8B illustrates an annotated version of the power profile of FIG. 8A.

FIG. 8A illustrates a power profile of an example ophthalmic device, the power profile showing optical power vs. radial distance from the center of ophthalmic device. As shown, a center zone 802 or region disposed at and/or adjacent a center of the ophthalmic lens has a positive optical power. The surface of the ophthalmic lens then exhibits a negative optical power at a radius outside of the center zone 802. However, a treatment zone 804 is illustrated at about 1.50 mm to 2.00 mm, where the optical power rises from the surrounding regions and exhibits a less negative optical power. As a further example, the treatment zone 804 may be configured as a treatment zone for treating, preventing, or slowing myopia progression. The treatment zone 804 may be configured to have a surface shape that exhibits a focal ring, with the locus of each of the infinite focal points on the ring being displaced ('non-coaxial') from the geometric axis of the center zone 802. Additional treatment zones 804 may be used. The at least one treatment zone 804 may have an annular configuration sharing a common geometric axis with the center zone 802. The at least one treatment zone 804 may have a surface shape comprising a portion of a generally toroidal shape, wherein the at least one treatment zone 804 is arranged as to form a continuous surface with the center zone. As an example, the portion of the toroidal shape to be utilized may be derived from a torus (e.g., a spheroidal torus), after making a slice in the shape of the surface of a right circular cone through the surface of the spheroidal torus wherein the principal axis of the cone is coincident with the axis of rotation about which the torus is generated.

FIG. 8B illustrates an annotated version of the power profile of FIG. 8A. As shown, the radial width and optical power of the center zone 802 may be configured to provide slowing, retarding or preventing of myopia progression, while providing satisfactory visual acuity. As a further example, the position of the treatment zone 804 relative to the center zone 802 may be customized.

Figure 8C:
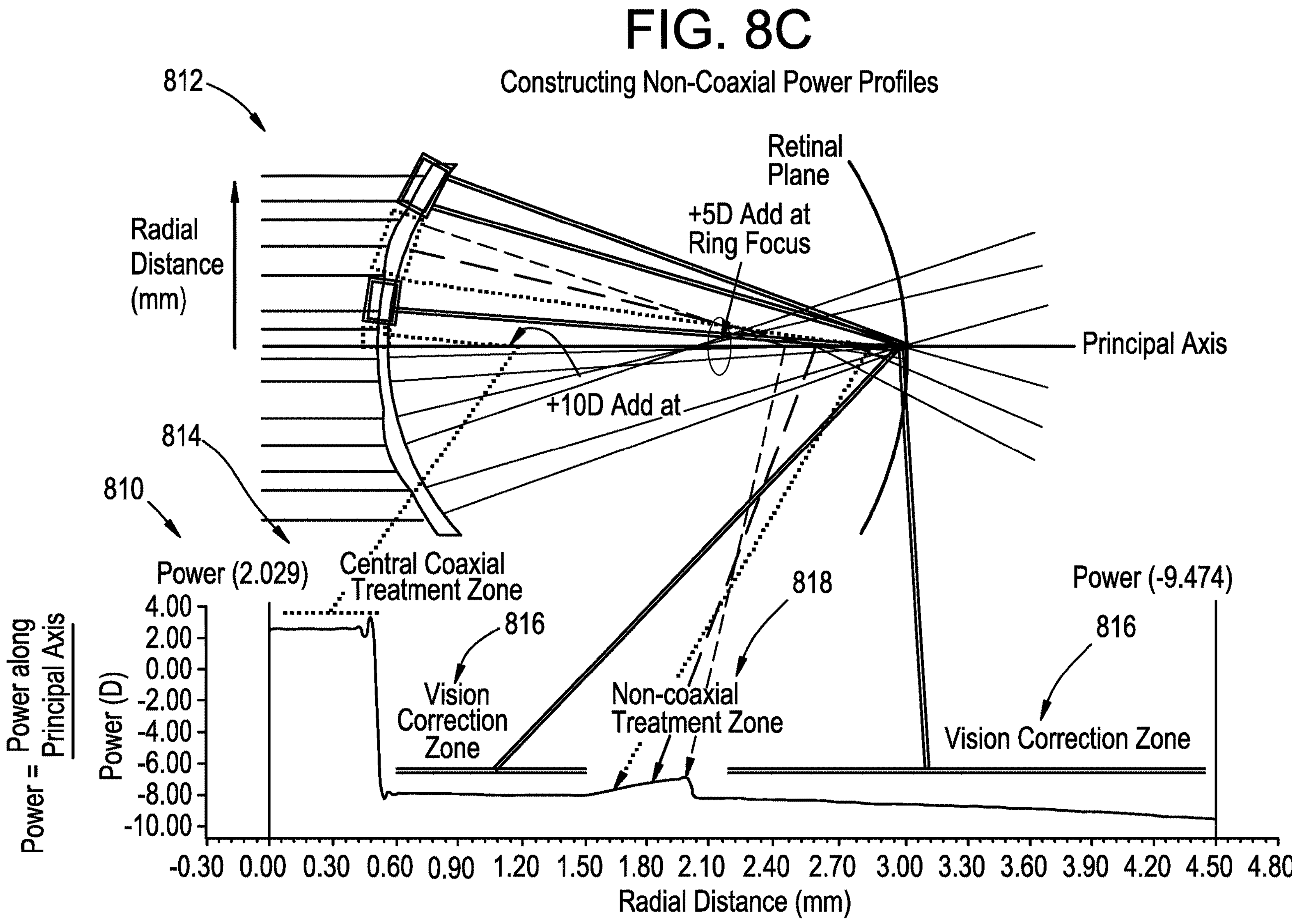
FIG. 8C illustrates a ray diagram showing coaxial and non-coaxial focal points associated with an ophthalmic device of the present disclosure.

FIG. 8C illustrates an annotated power profile 810 in reference to a respective ray diagram 812. The ray diagram 812 relates to a lens design in accordance with an aspect of the present disclosure. As shown, the lens design exhibits a particular ray pattern (e.g., refraction) based on the incident light on the lens. As an example, a central coaxial treatment zone 814 may be generated by configuring a central ADD power region exhibiting convergence of incident rays to an on-axis focal point that is disposed between the lens and the retinal plane of a wearer. One or more vision correction zones 816 may be generated by configuring the lens to exhibit convergence of incident rays to an on-axis focal point at or near the retinal plane. A non-coaxial treatment zone may be generated by configuring an ADD power region exhibiting convergence of incident rays to a ring of off-axis foci that is disposed between the lens and the retinal plane of a wearer. It is understood that the ADD power may reference a positive optical power relative to an adjacent region and/or the vision correction zone 816.

Figure 9A:
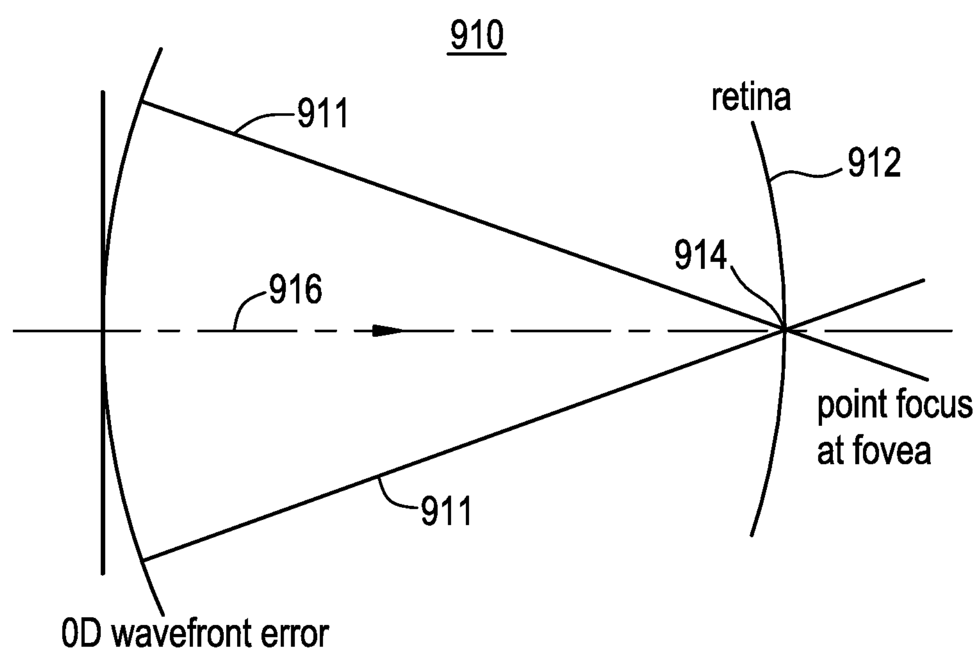
FIG. 9A is a diagrammatic representation of rays associated with a plane wavefront passing through an emmetropic (or fully corrected) eye towards the retina.

Referring to FIG. 9A, there is illustrated rays associated with a wavefront passing through an emmetropic (or fully corrected) eye 910. The rays derive from a plane wavefront (that is, with 0.00 D spherical power) outside the eye and travel through the optics of the eye and any corrective device towards the retina 912. As illustrated, assuming the system has zero wavefront aberrations, rays 911 of this wavefront focus at a single focal point 914 along the optical axis 916. Given that this is a wavefront error representation for a fully corrected eye, the focal point 914 is on the fovea which is located at the center of the macula lutea of the retina 912. The fovea is the area of the retina responsible for sharp central vision.

Figure 9B:
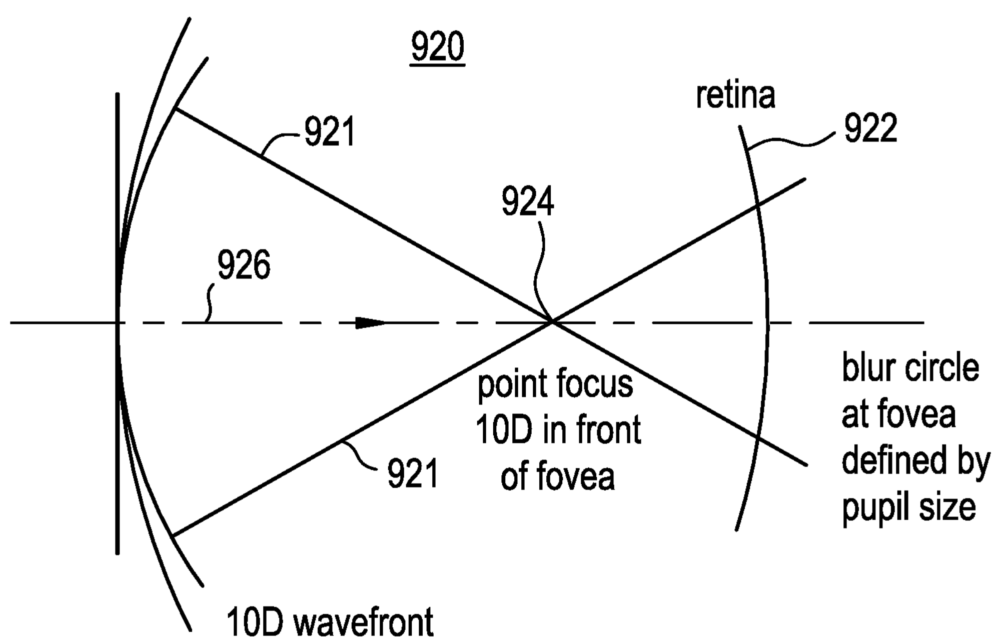
FIG. 9B is a diagrammatic representation of rays associated with a wavefront with +10.00 D of spherical wavefront error (relative to that in FIG. 9A) travelling through the eye towards the retina.

In contrast, in FIG. 9B, there is illustrated rays 921 from a wavefront with +10.00 D of spherical wavefront error (relative to an emmetropic or fully corrected eye), as they would travel through the eye and any optical device towards the retina 922 of the eye 920. As illustrated, the wavefront focuses at a single point 924 along the optical axis 926 in front of the retina 922 as would be expected with a +10.00 D defocus. Consistent with conventional spherical optics, the optics of the lenses are designed with a primary optical axis. The light rays converge towards a single point, namely, the focal point which lies on this axis. The amount of spherical wavefront error dictates the location of the focal point, on or in front of the fovea of the retina, as the examples illustrate in FIGS. 9A and 9B respectively. These two figures may be utilized to set the basic parameters/principles upon which the description of the present invention is based; however, it should be understood that while only spherical refractive errors are illustrated and described for ease of explanation, the present invention is equally applicable to toric lenses which include cylindrical powers at a specific axis. In addition, as set forth in greater detail subsequently, the treatment zones may include a cylinder power and axis, and they may also comprise more complex optical designs such as higher order aberrations.

Figure 9C:
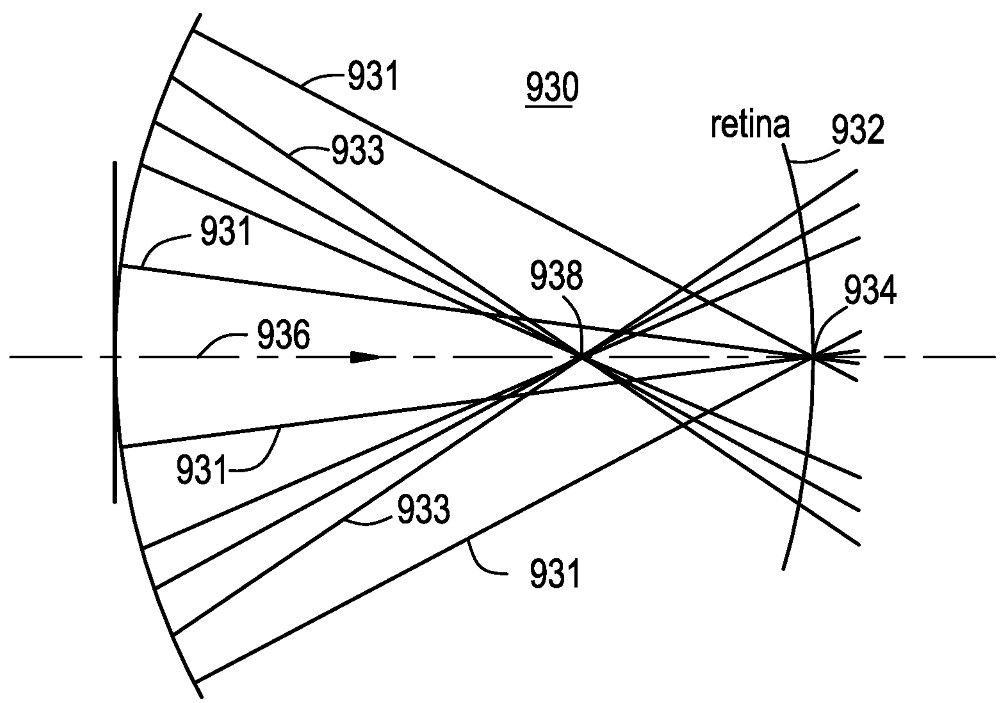
FIG. 9C is a diagrammatic representation of rays passing through an optical system (emmetropic eye plus optical device) where the optical device has plano (that is, 0.00 D) power in the center and +10.00 D coaxial power in the periphery.

FIG. 9C illustrates rays derived from a plane wavefront external to an emmetropic eye passing through an optical system (eye plus optical device) where the optical device has plano (that is, 0.00 D) power in the center 931 and +10.00 D coaxial power in the periphery (that is, a 'coaxial' treatment zone) 933, as they would travel through the eye 930 towards the retina 932. Those skilled in the art will understand that the illustration and those following could also be adapted to apply to an ametropic eye where the central power of the device is corrective for the refractive error and the peripheral power remains at +10.00 D relative to the central power (+10.00 D ADD). As illustrated, rays passing through the central portion of the device focus at a single point 934 along the primary optical axis 936. Given that this is a representation of an emmetropic eye, the focal point 934 is on the fovea of the retina 932. Rays 933 passing through the treatment zone may focus at a single point 938 in front of the retina 932 as would be expected with a +10.00 D defocus. Concentric or aspheric multifocal lens designs typically have both primary distance power and ADD power having a common axis. Also, in these applications to maintain optimum image quality, the ADD power is usually limited to a range of about +1.00 to +3.00 D. Accordingly, high ADD power may not work with this arrangement of coaxial treatment zones, but rather a non-coaxial arrangement, as set forth in detail subsequently, may be used.

Figure 9D:
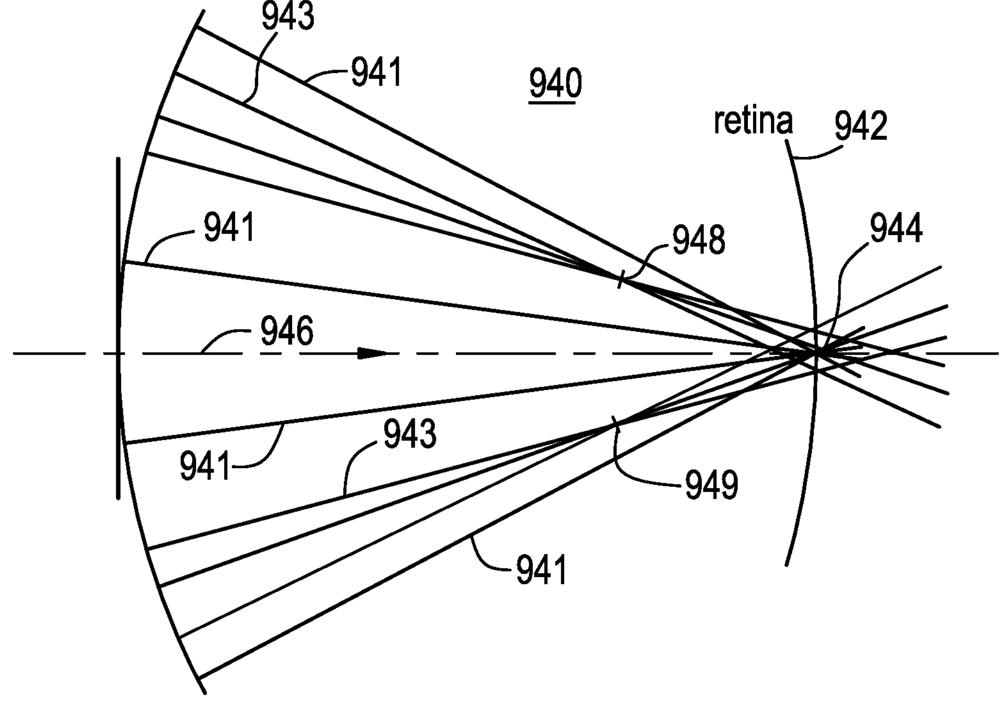
FIG. 9D is a diagrammatic representation of rays passing through an optical system (emmetropic eye plus optical device) where the optical device has plano (that is, D) power in the center and +10.00 D non-coaxial power in the periphery.

FIG. 9D illustrates rays derived from a plane wavefront external to the eye passing through an optical system (eye plus optical device) where the optical device has plano (that is, 0.00 D) power in the center 941 and +10.00 D non-coaxial power in the periphery (that is, a 'non-coaxial' treatment zone) 943, as they would travel through the eye 940 towards the retina 942. As illustrated, rays passing through the central portion of the device focus at a single point 944 along the primary optical axis 946. Given that this is a representation of an emmetropic eye, the focal point 944 is on the fovea of the retina 942. Rays 943 passing through the treatment zone focus at single points 948 and 949, in this cross-sectional illustration, in front of the retina 942 as would be expected with a +10.00 D lens. However, these cones of rays are now directed towards the fovea unlike as illustrated in FIG. 9C where the rays strike the retina at some distance from the fovea. The treatment zone now has focal points 948 and 949 that do not coincide with the original common optical axis 946 (that is, the principal axis of the optical system) and are therefore non-coaxial. It is important to note that the rays passing through the non-coaxial treatment zones come to a focal point +10.00 D in front of the retina 942 along their own axes; however, the center rays of each of the non-coaxial treatment zones cross the principal axis at the fovea and, therefore, individually have no power error.

Figure 9E:
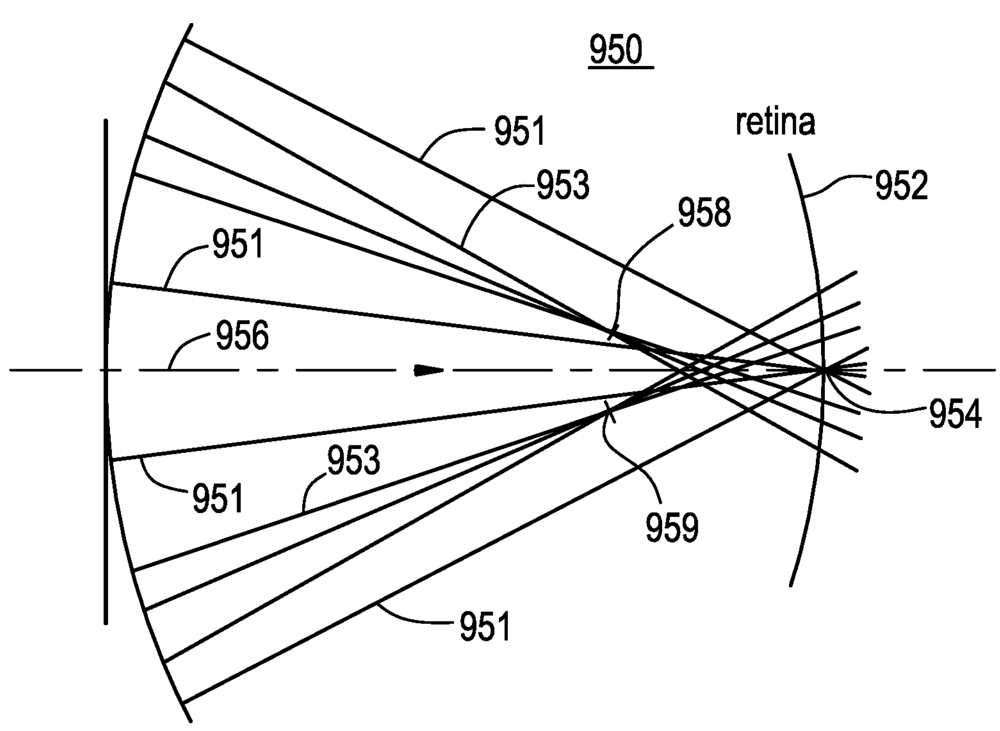
FIG. 9E is a diagrammatic representation of rays passing through an optical system (emmetropic eye plus optical device) where the optical device has plano (that is, D) power in the center and +10.00 D non-coaxial power in the periphery with a center of the ray bundle from this peripheral zone tilted inward and directed away from the fovea.

FIG. 9E illustrates rays derived from a plane wavefront external to the eye passing through an optical system (eye plus optical device) where the optical device has plano (that is, 0.00 D) power in the center 951 and +10.00 D non-coaxial power in the periphery (that is, a 'non-coaxial' treatment zone) 953, as they would travel through the eye 950 towards the retina 952. As illustrated, rays passing through the central portion of the device focus at a single point 954 along the primary optical axis 956. Given that this is a representation of an emmetropic eye, the focal point 954 is on the fovea of the retina 952. Rays 953 passing through the treatment zone focus at single points 958 and 959, in this cross-sectional illustration, in front of the retina 952 as would be expected with a +10.00 D lens. However, these cones of rays are now directed symmetrically away from the fovea. Once again, the treatment zone has focal points 958 and 959 that do not coincide with the original common optical axis 956 (that is, the principal axis of the optical system) and are therefore non-coaxial. It is important to note that the rays passing through the non-coaxial treatment zone come to a focal point +10.00 D in front of the retina 952 along their own axis but have different direction or slope (that is, 'tilt') than the treatment zone of FIG. 9D to direct the center rays symmetrically away from the fovea. In addition, the treatment zone axes converge symmetrically towards the principal axis 956. In other words, the treatment zone directs light rays across the original common optical axis 956 towards peripheral sections of the retina 952 equidistant from the fovea, a symmetrical arrangement in this two-dimensional representation and which forms a blur ring on the retina in three-dimensional space.

It is important to note that combinations of the above described configurations are also possible, for example, an optical design which includes a base sphere as myopia correction zone, a treatment zone that directs central rays of the zone to cross the optical axis in front of the retina, and a treatment zone that directs central rays of the zone to cross the optical axis behind the retina. The principles embodied in these descriptions may also apply to devices with multiple treatment zones.

Incorporated herein also are designs that have negative ADD power for reduction of hypermetropia in young children. Now the distance correction zone may have positive power, e.g., from +0.25 to +20.00 D. The same principle that applies to myopia control applies here, in that the wearer of the device should not use the ADD section of the device for near or distance vision but rather use the hypermetropic distance correction for all viewing. The non-coaxial nature of the ring focus prevents the user from accommodating to look through the treatment region for vision. The negative ADD power (e.g., from −0.25 to −20.00 D) then serves to stimulate eye growth to reduce the degree of hypermetropia.

Figure 10A:
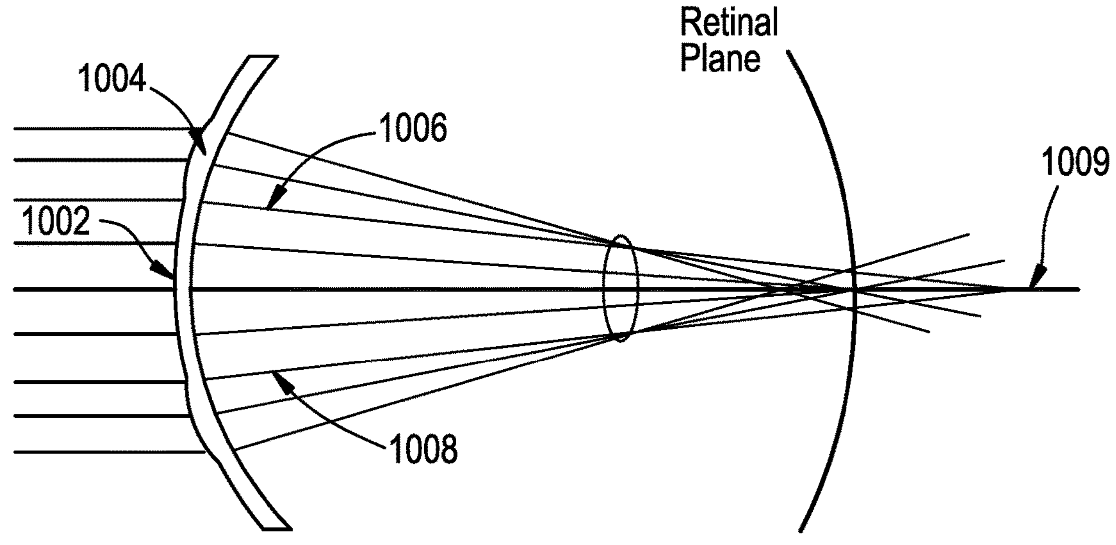
FIG. 10A illustrates a ray diagram showing a focal ring of an ophthalmic device in accordance with the present disclosure.

FIG. 10A illustrates a ray diagram of an ophthalmic lens in accordance with the present disclosure. As shown, a peripheral zone or treatment zone 1004 is shown surrounding a center myopia correction zone 1002. The annular treatment zone 1004 comprises a generally toroidal shape (e.g., a portion of a torus), a cross-section of which is illustrated in FIG. 10A. The treatment zone 1004 is configured to result in a focal ring, which is generated in front of a retinal plane of a wearer of the ophthalmic device, such as between the ophthalmic lens and the retinal plane. As shown, an innermost ray 1006 of treatment zone 1004 along with a corresponding (opposite position about the annulus) innermost ray 1008 are configured to converge to a point 1009 that is behind the retinal plane.

Figure 10B:
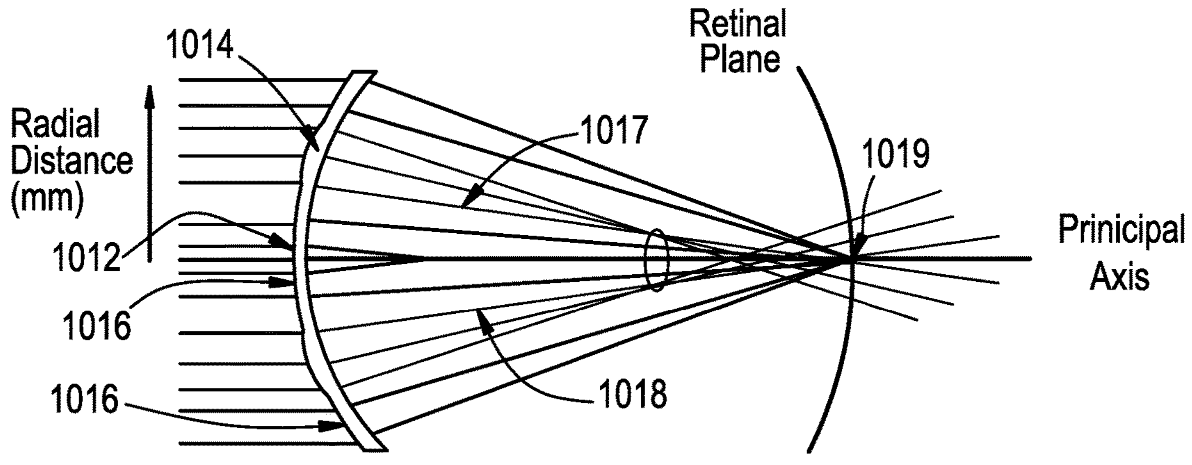
FIG. 10B illustrates a ray diagram showing a focal ring of an ophthalmic device and a center zone with ADD power in accordance with the present disclosure.

FIG. 10B illustrates a ray diagram of an ophthalmic lens in accordance with the present disclosure. The lens incorporates correction for myopia 1016. The lens also incorporates a central treatment zone 1012 and a peripheral treatment zone 1014 radially displaced from the central treatment zone 1012. The treatment zone 1014 comprises a portion of a generally toroidal shape, a cross-section of which is illustrated in FIG. 10B. The center zone 1012 is shown comprising a surface structure that is configured to produce a coaxial point focus, at a position consistent with the ADD power of that zone. The treatment zone 1014 is configured to exhibit (that is, result in) a focal ring, which is generated in front of a retinal plane of a wearer of the ophthalmic device, such as between the ophthalmic lens and the retinal plane. One or more myopia correction zones 1016 may be configured with a negative optical power and may exhibit a focal point that is coaxial with principal axis of the lens including with focal point generated by the center zone 1012. As shown, the treatment zone 1014 has an annular configuration and an innermost ray 1017 along with a corresponding (opposite position about the annulus) innermost ray 1018 are configured to converge to a point 1019 that is at an intersection of the retinal plane and the principal axis.

Figure 11A:
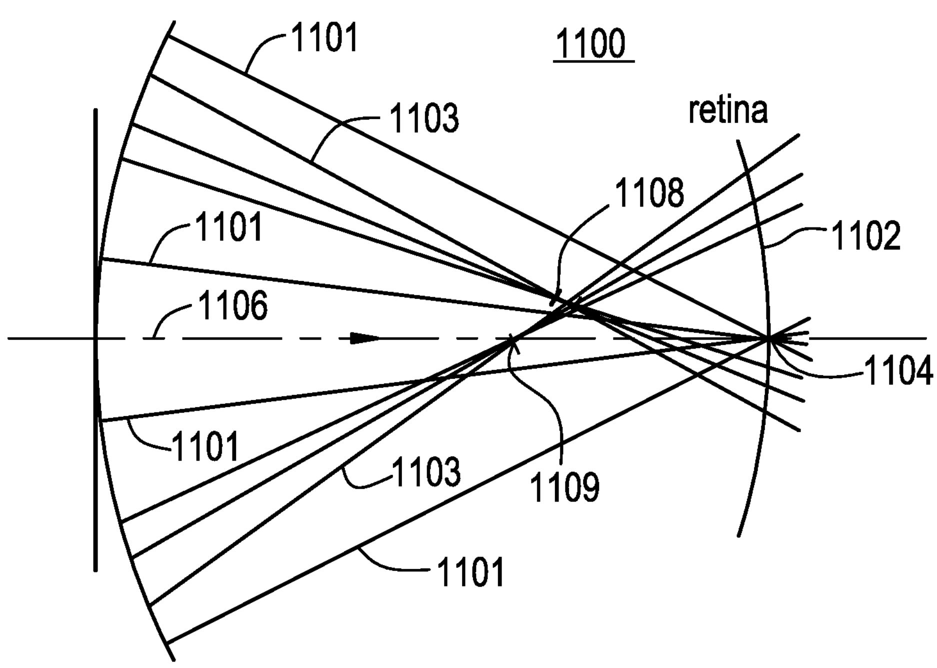
FIG. 11A is a diagrammatic representation of rays passing through an optical system (emmetropic eye plus optical device) where the optical device has plano (that is, 0.00 D) power in the center and +10.00 D non-coaxial power in the periphery with a center of the ray bundle of the peripheral zone tilted inward and directed away from the fovea in an asymmetric manner.

FIG. 11A illustrates rays derived from a plane wavefront external to the eye passing through an optical system (eye plus optical device) where the optical device has plano (that is, 0.00 D) power in the center 1101 and +10.00 D non-coaxial power in the periphery (that is, a 'non-coaxial' treatment zone) 1103, as they would travel through the eye 1100 towards the retina 1102. As illustrated, rays passing through the central portion of the device focus at a single point 1104 along the primary optical axis 1106. Given that this is a representation of an emmetropic eye, the focal point 1104 is on the fovea of the retina 1102. Rays 1103 passing through the treatment zone come to local point foci at 1108 and 1109 in this cross-sectional illustration, in front of the retina 1102, as would be expected with a +10.00 D lens, but asymmetrically away from the fovea. The treatment zone may create a focal ring (or ellipse) including a focal point 1108 that does not coincide with the original common axis (e.g., primary optical axis 1106) and is therefore non-coaxial, and another focal point 1109 that coincides with the original common axis, a coaxial focus. It is important to note that rays from any small bundle passing through the treatment zone will focus along their own axis and these may have different slopes (tilt) within the treatment zone.

Figure 11B:
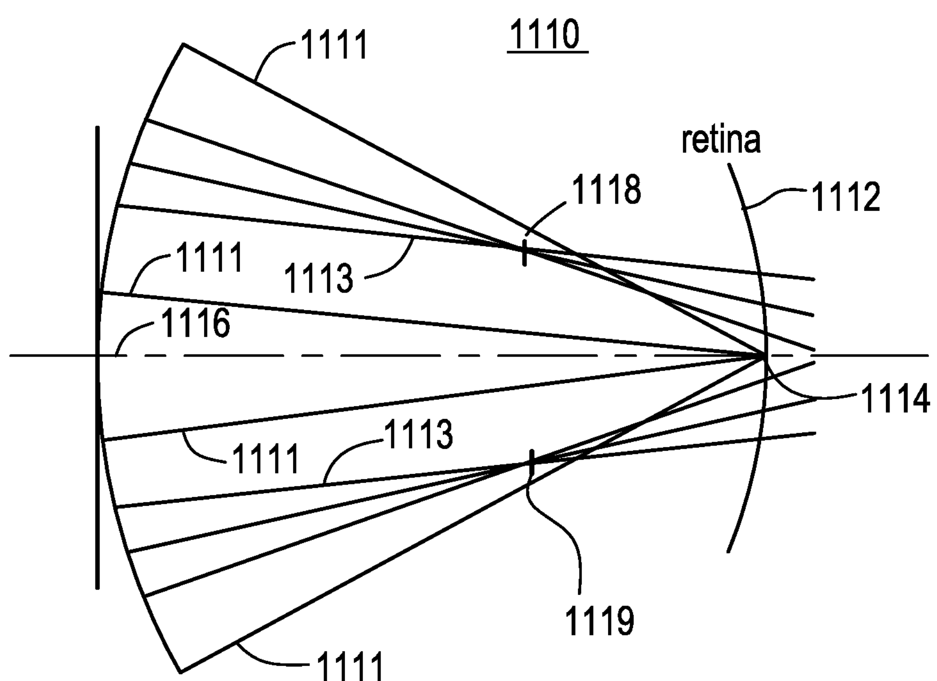
FIG. 11B is a diagrammatic representation of rays passing through an optical system (emmetropic eye plus optical device) where the optical device has plano (that is, 0.00 D) power in the center and +10.00 D non-coaxial power in the periphery with a center of the ray bundle of the peripheral zone tilted outward and directed away from the fovea in a symmetric manner.

FIG. 11B illustrates rays derived from a plane wavefront external to the eye passing through an optical system (eye plus optical device) where the optical device has plano (that is, 0.00 D) power in the center 1111 and +10.00 D non-coaxial power in the periphery (that is, a 'non-coaxial' treatment zone) 1113, as they would travel through the eye 1110 towards the retina 1112. As illustrated, rays passing through the central portion of the device focus at a single point 1114 along the primary optical axis 1116. Given that this is a representation of an emmetropic eye, the focal point 1114 is on the fovea of the retina 1112. Rays 1113 passing through the treatment zone come to local point foci at 1118 and 1119 in this cross-sectional illustration, in front of the retina 1112, as would be expected with a +10.00 D lens. The treatment zone may create a focal ring including focal points 1118 and 1119 that do not coincide with the original common axis (e.g., primary optical axis 1116) and are therefore non-coaxial. It is important to note that rays passing through the treatment zone focus along their own axis and have different slopes (tilt) than the treatment zone of FIG. 9D to direct the central rays of the treatment zone symmetrically away from the fovea but still have a local point focus of +10.00 D in front of the retina 1112. In addition, the central rays from the treatment zone converge symmetrically behind the focus of the myopia correction zone 1114. In other words, the treatment zone directs light rays such that they cross the original primary optical axis 1116 outside the eye in a symmetric manner.

Figure 11C:
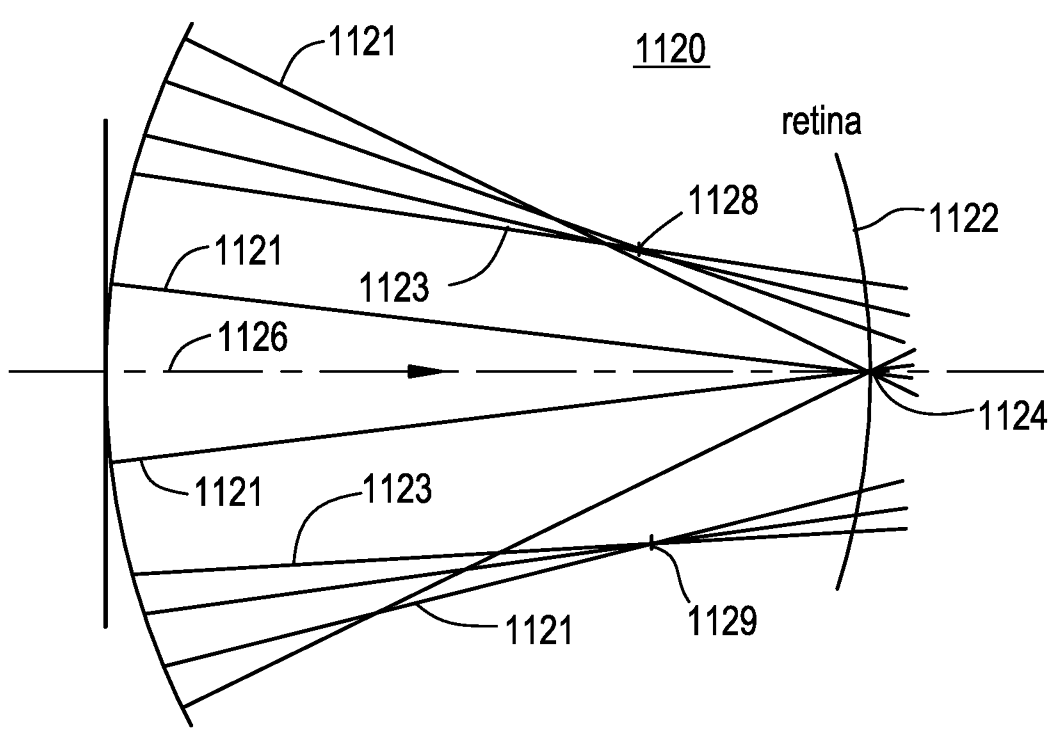
FIG. 11C is a diagrammatic representation of rays passing through an optical system (emmetropic eye plus optical device) where the optical device has plano (that is, 0.00 D) power in the center and +10.00 D non-coaxial power in the periphery with a center of the ray bundle of the peripheral zone tilted outward and directed away from the fovea in an asymmetric manner.

FIG. 11C illustrates rays derived from a plane wavefront external to the eye passing through an optical system (eye plus optical device) where the optical device has plano (that is, 0.00 D) power in the center 1121 and +10.00 D non-coaxial power in the periphery (that is, a 'non-coaxial' treatment zone) 1123, as they would travel through the eye 1120 towards the retina 1122. As illustrated, rays passing through the central portion of the device focus at a single point 1124 along the primary optical axis 1126. Given that this is a representation of an emmetropic eye, the focal point 1124 is on the fovea of the retina 1122. Rays 1123 passing through the treatment zone come to local point foci at 1128 and 1129 in this cross-sectional illustration, in front of the retina 1122, as would be expected with a +10.00 D lens, but asymmetrically away from the fovea. The treatment zone may create a focal ring (or ellipse) including focal points 1128 and 1129 that do not coincide with the original common axis (e.g., primary optical axis 1126) and are therefore non-coaxial. It is important to note that rays from any small bundle passing through the treatment zone will focus along their own axis and these may have different slopes (tilt) within the treatment zone. In other words, the treatment zone directs light rays such that they cross the original common optical axis e.g., primary optical axis 1126 outside the eye in an asymmetric manner.

Combinations of the above described configurations are also possible, for example, an optical design which includes a base sphere as myopia correction zone, treatment zones that direct rays across the primary optical axis, and treatment zones that direct rays to the same side of the primary optical axis.

Figure 12A:
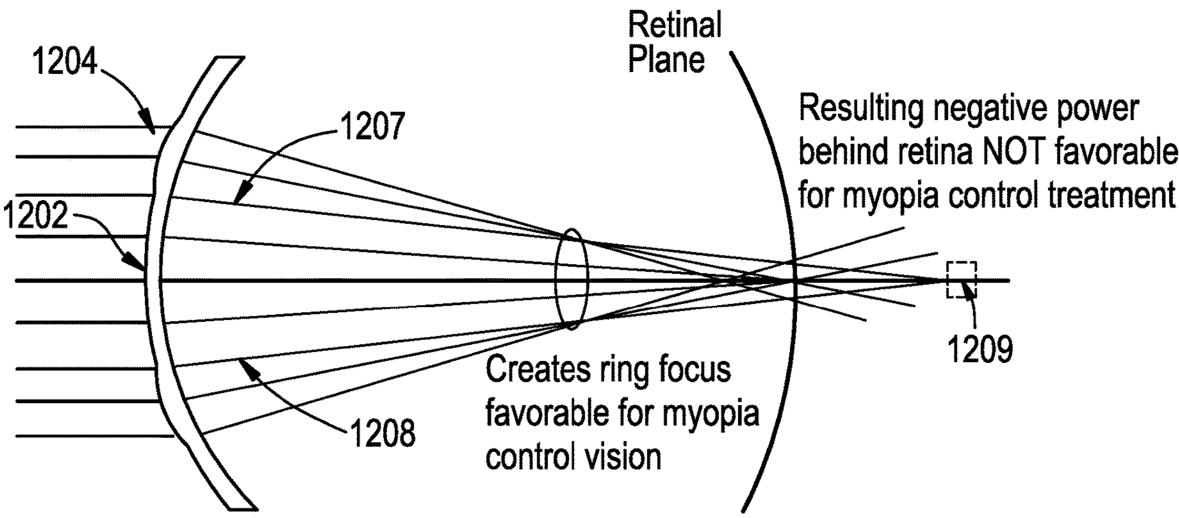
FIG. 12A illustrates a ray diagram showing a focal ring of an ophthalmic device exhibiting rays passing through the peripheral zone that converge to a point behind the retinal plane in accordance with the present disclosure.

FIG. 12A illustrates a ray diagram of an ophthalmic lens in accordance with the present disclosure. As shown, a peripheral zone or treatment zone 1204 is shown surrounding a center zone 1202. The annular treatment zone 1204 comprises a portion of a generally toroidal shape, a cross-section of which is illustrated in FIG. 12A. The treatment zone 1204 is configured to exhibit (result in) a focal ring, which is generated in front of a retinal plane of a wearer of the ophthalmic device, such as between the ophthalmic lens and the retinal plane. As shown, an innermost ray 1206 of the treatment zone 1204 along with a corresponding (opposite position about the annulus) innermost ray 1208 are configured to intersect at a point 1209 that is behind the retinal plane. As such, part of the biconic shape that represents the volume in which there is intersection of rays passing through the treatment zone falls behind the retina.

Figure 12B:
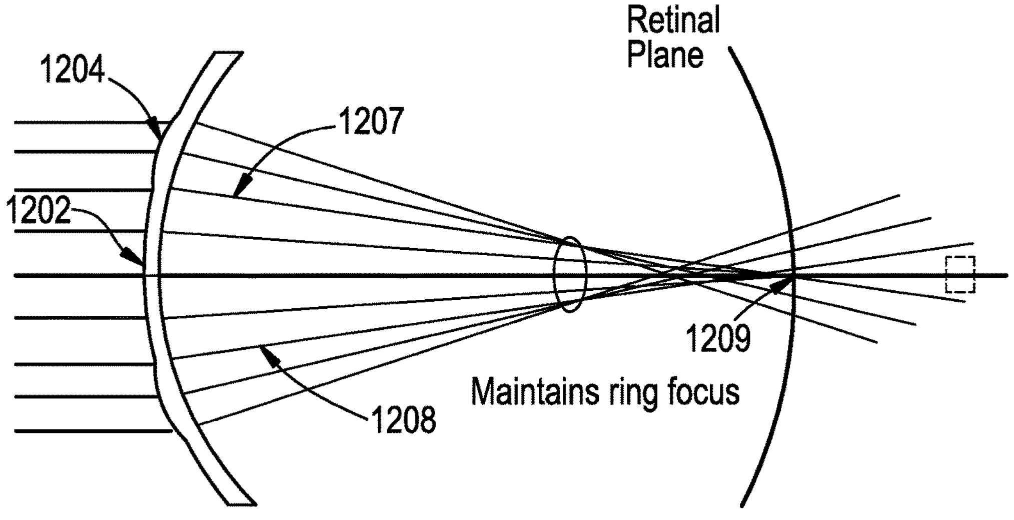
FIG. 12B illustrates a ray diagram showing a focal ring of an ophthalmic device exhibiting rays passing through the peripheral zone that do not converge at any point behind the retinal plane in accordance with the present disclosure.

However, the surface of the treatment zone 1204 may be configured (e.g., tilted such that the rays are directed by the lens toward or away from the central or principal axis) to minimize the convergence of the rays behind the retinal plane of a wearer, as illustrated in FIG. 12B. As shown in FIG. 12B, an innermost ray 1207 passing through the annular treatment zone 1204 along with the corresponding (opposite position about the annulus) innermost ray 1208 are configured to converge at a point 1209 at an intersection of the retinal plane and the principal axis of the lens. Such tilt control may be used to configure an innermost ray to cross the principal axis between the retinal plane or in front of the retinal plane. Now, no part of the biconic shape that represents the volume in which there is intersection of rays passing through the treatment zone falls behind the retina. The location of the convergence of these rays should be configured to minimize visual disturbance, such as would happen if the treatment zone 1204 were configured to generate a coaxial point focus.

Figure 13:
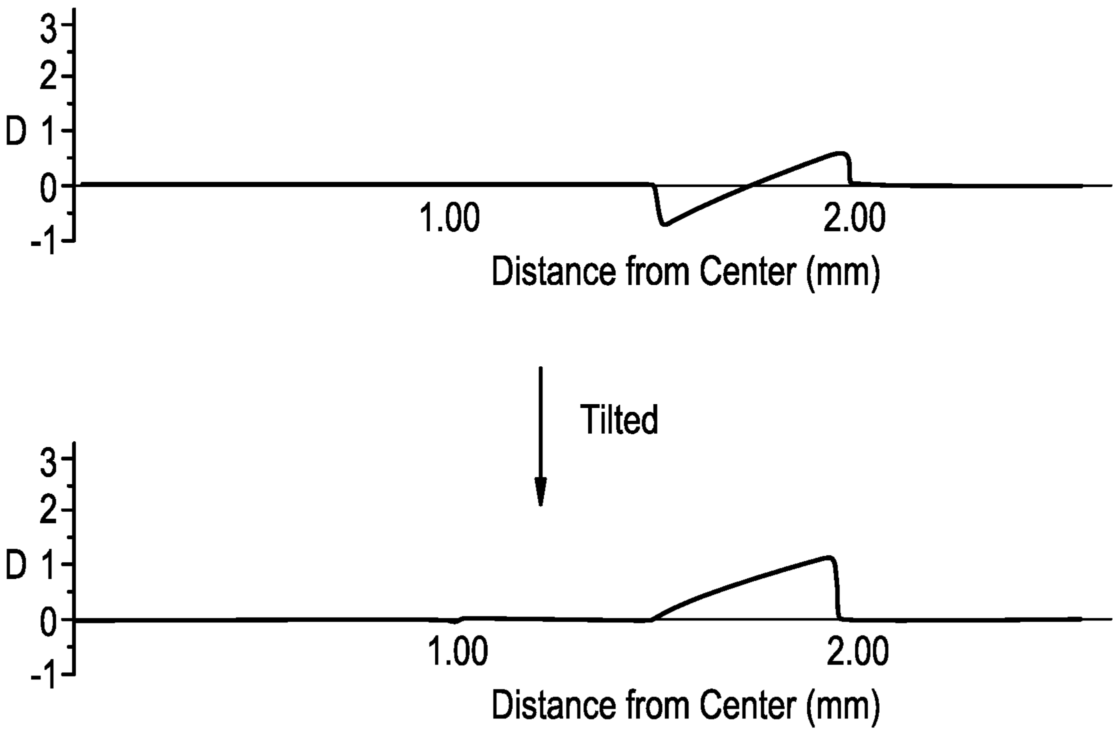
FIG. 13 illustrates a comparison of two power profiles of respective ophthalmic devices in accordance with the present disclosure.
Figure 14A:
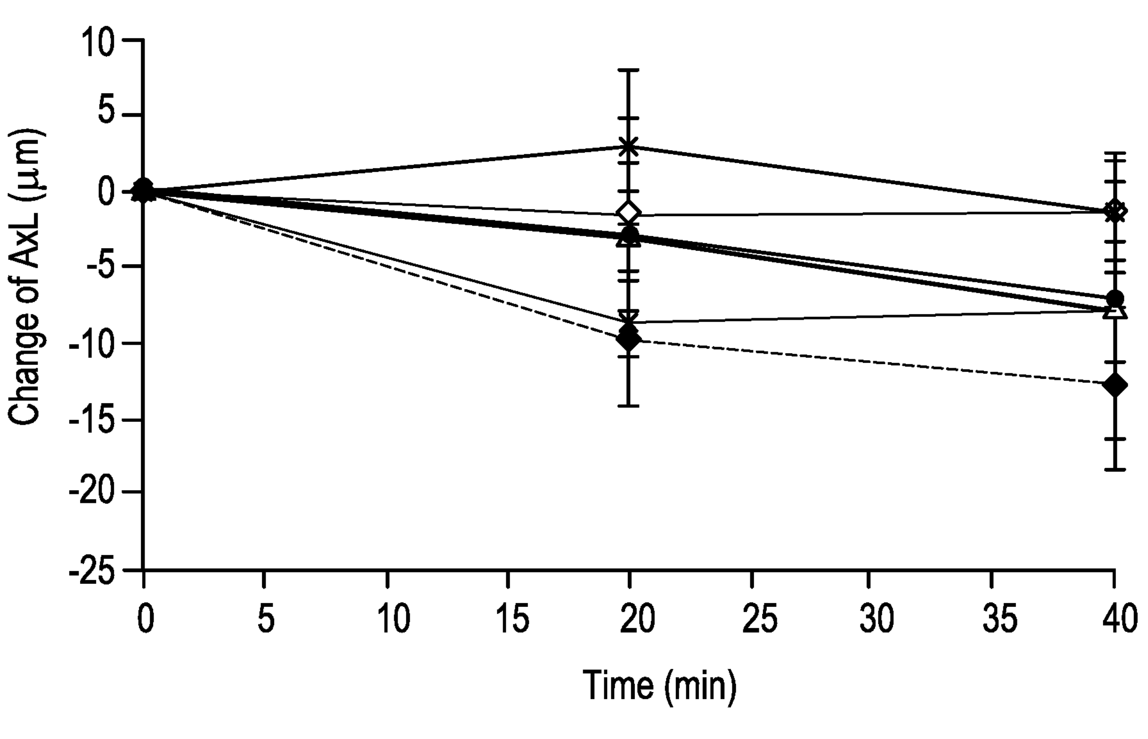
FIG. 14A illustrates a plot of change of axial length of human eyes exposed to various sample optical configurations.
Figure 14B:
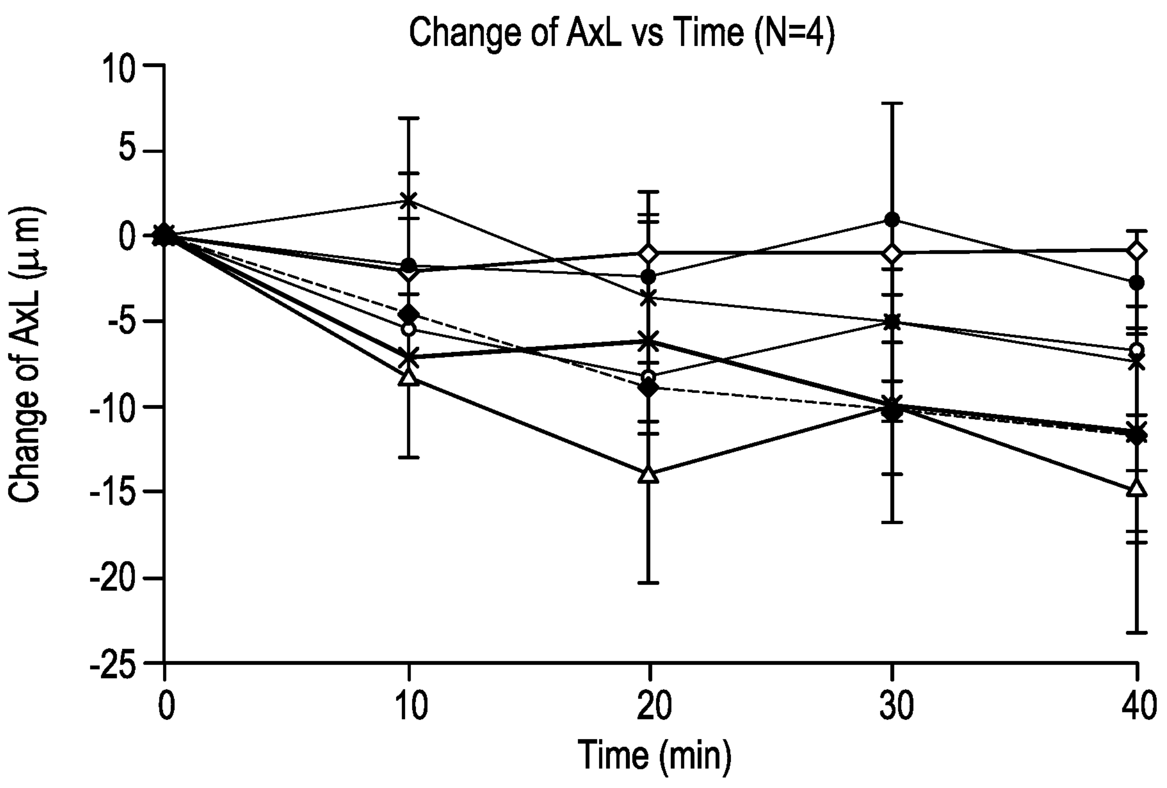
FIG. 14B illustrates a plot of change of axial length of human eyes exposed to various sample optical configurations.
Figure 14C:
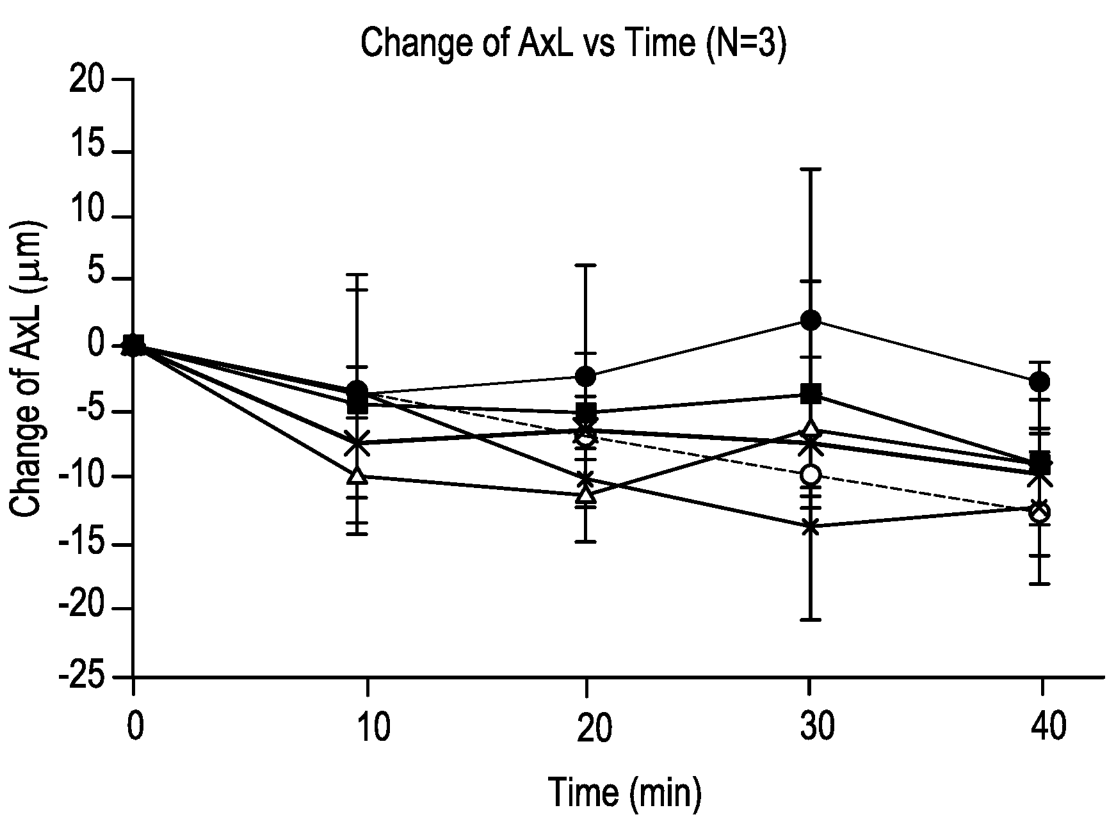
FIG. 14C illustrates a plot of change of axial length of human eyes exposed to various sample optical configurations.
Figure 14D:
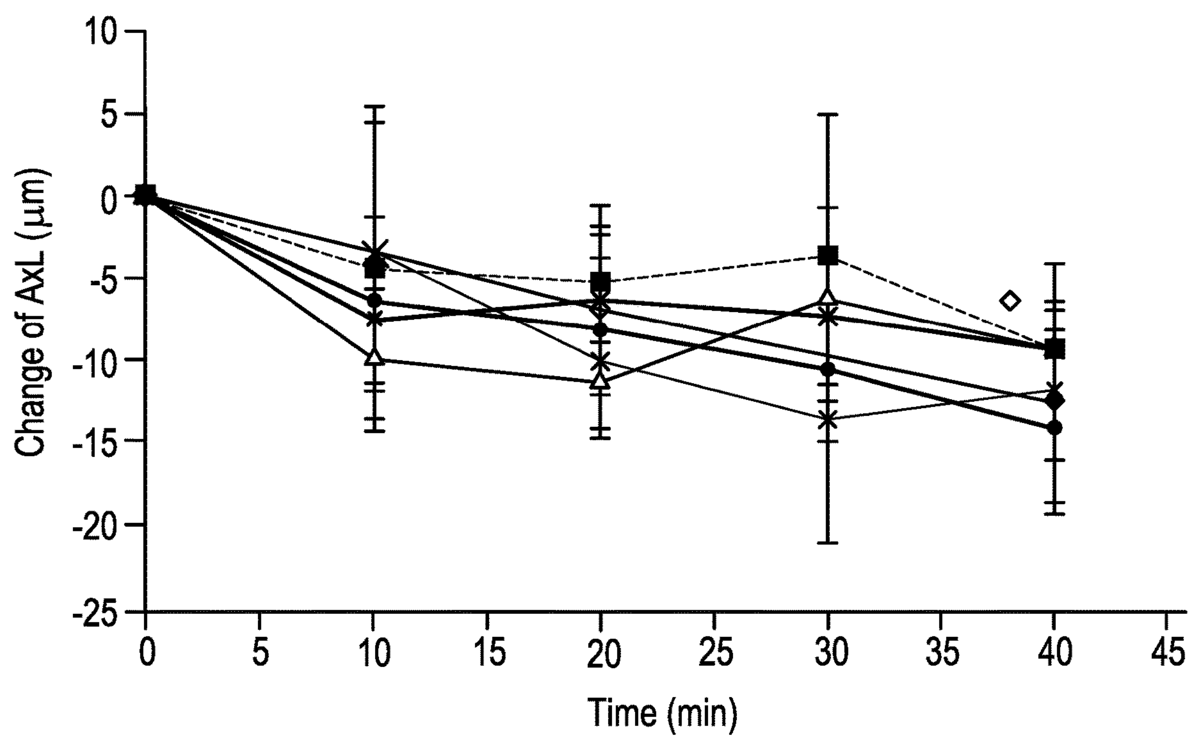
FIG. 14D illustrates a plot of change of axial length of human eyes exposed to various sample optical configurations.

To further illustrate the "tilting" configuration of the treatment zone 1204, FIG. 13 shows a comparison between two power profiles of respective ophthalmic devices, wherein the "tilted" treatment zone minimizes a negative power dip in the power profile. Further, the power profile of the treatment zone may have a curvilinear (e.g., convex) shape to bring about the ring focus.

As an illustrative example, favorable results were achieved using tilt angles between +0.035 and +0.3215 degrees relative to a zero-angle comparator. The angle of tilt is designated as zero where a central (mid annulus) ray of the treatment zone passes through the intersection of the retinal plane and the central or principal axis (as in FIG. 12A). A positive direction for tilt results in a central (mid annular) ray of the treatment zone intersecting with the principal axis in front of the retina, whereas a negative direction for tilt results in a central (mid annular) ray of the treatment zone intersecting with the principal axis behind the retina. It is understood that other positive angles and/or negative angles of tilt may be used.

As a further example, particular lens designs were tested using a choroidal thickness model for predicting their potential myopia control effect. In this model, human eyes are exposed to optical configurations for a period of time and the axial length of the eye is monitored. Choroidal thickness will remain relatively constant in the absence of any change in optical stimulus over the short time periods studied. Optical configurations that are likely to have a myopia control effect are accompanied by an increase in choroidal thickness and corresponding reduction in apparent axial length of the eye as measured by partial coherence interferometry. Conversely, optical configurations that are likely to exacerbate myopia progression are accompanied by a decrease in choroidal thickness and corresponding increase in apparent axial length of the eye. For example, Read et al. have shown that exposure to a +3 D single vision lens resulted in an apparent reduction in axial length, whereas a −3 D lens resulted in apparent axial elongation (Read S A, Collins M J, Sander B P. Human optical axial length and defocus. Invest Ophthalmol Vis Sci. 2010 December; 51(12):6262-9.) In animal models, manipulation of the visual environment with positive lenses results in reduced eye growth and with negative lenses results in increased eye growth and myopia.

It is important to note various design configurations are envisioned by varying the power, size, location and tilt of treatment zones as set forth below, and as shown in FIGS. 14, and 16 to 20:

Non-Coaxial+5 D Design (2 Rings)

- Ring 1=+5 D non-coaxial power; 1.87 to 3.43 mm diameter zone: +0.109 degree tilt
- Ring 2=+5 D non-coaxial power; 4.45 to 9.00 mm diameter zone: +0.321 degree tilt Non-Coaxial+5 D Design (1 Ring with 1.00 mm Center+10 D Region)

- Ring=+5 D non-coaxial power; 3.00 to 4.00 mm diameter zone: +0.066 degree tilt Non-Coaxial+2.5 D Design (1 Ring with 1.00 mm Center+5 D Region)

- Ring=+2.5 D non-coaxial power; 3.00 to 4.00 mm diameter zone: +0.035 degree tilt Non-Coaxial+5 D to +10 D Design (4 Rings with 1.00 mm Center+10 D Region)

- Ring 1=+5 D non-coaxial power; 3.00 to 4.00 mm diameter zone: +0.066 degree tilt
- Ring 2=+10 D non-coaxial power; 6.00 to 7.00 mm diameter zone: +0.131 degree tilt
- Ring 3=+10 D non-coaxial power; 7.00 to 8.00 mm diameter zone: +0.129 degree tilt
- Ring 4=+10 D non-coaxial power; 8.00 to 9.00 mm diameter zone: +0.129 degree tilt Non-Coaxial+5 D Design (1 Ring)

Ring=+5 D non-coaxial power; 3.00 to 4.00 mm diameter zone: +0.066 degree tilt

Non-Coaxial+7 D Design (2 Rings)

Ring 1=+7 D non-coaxial power; 3.40 to 4.80 mm diameter zone: +0.132 degree tilt Ring 2=+7 D non-coaxial power; 6.80 to 8.30 mm diameter zone: +0.140 degree tilt Non-Coaxial+7 D Design (2 Rings with 1.20 mm Center+10 D Region)

Ring 1=+7 D non-coaxial power; 2.80 to 4.00 mm diameter zone: +0.111 degree tilt Ring 2=+7 D non-coaxial power; 6.50 to 8.00 mm diameter zone: +0.142 degree tilt Results for a series of lens designs are illustrated in FIGS. 14A-14D. In each of these experiments, +3 D defocus is used as a comparator. As can be observed, optical configurations as described in the current disclosure can exhibit similar to or larger than the projected myopia control effect in response to +3 D defocus. The results of these experiments demonstrate that positive powered treatment zones can result in an apparent decrease in axial length of the eye, that the effect increases with increasing ADD power, that non-coaxial designs are effective in myopia control and that refining tilt can enhance myopia control.

Figures 15A, 15B:
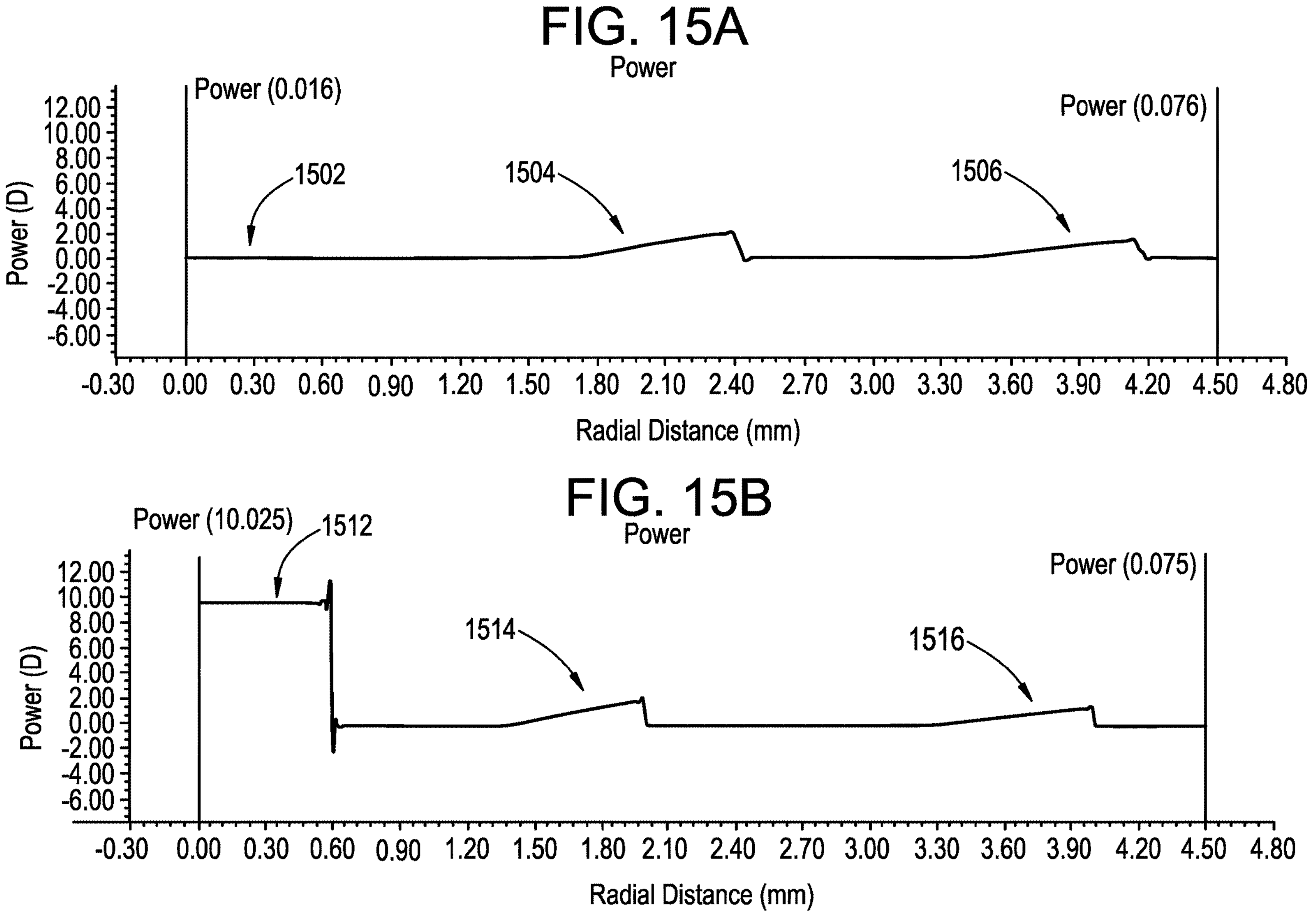
FIG. 15A illustrates a power profile of an ophthalmic device having two peripheral treatment zones in accordance with the present disclosure.
FIG. 15B illustrates a power profile of an ophthalmic device having two peripheral treatment zones and a center treatment zone with ADD power in accordance with the present disclosure.

Additionally, as shown below, the tilt angle may be applied to the central ray of the treatment zone in order to have all rays passing through that zone crossing the axis at or in front of the fovea (zero or positive power). This means the angle will change with zone power, zone displacement from the principal axis, and also zone width (e.g., a larger tilt is needed if the zone width and/or local individual axis power are increased). As described, the degree of tilt is measured relative to a zero angle comparator where a central (mid annulus) ray of the treatment zone pass through the intersection of the retinal plane and the central or principal axis:

FIG. 15A illustrates a conventional power profile of an example ophthalmic device, the power profile showing optical power vs. radial distance from the center of the ophthalmic device. As shown, a center zone 1502 or region disposed at and/or adjacent to the center of the ophthalmic lens has a generally flat optical power profile 1502. In this example, this zone has zero power and thus would represent an example for an emmetropic eye, but it is readily appreciable that the entire power profile of this zone may be adjusted to correct myopic refractive error. A first treatment zone 1504 is illustrated at about 1.80 mm to 2.40 mm, where the optical power rises from the surrounding regions and exhibits a more positive optical power. A second treatment zone 1506 is illustrated at about 3.40 mm to 4.20 mm, where the optical power rises from the surrounding regions and exhibits a more positive optical power. The conventional power profile derives the power for a given radial distance from the center of the lens from the inverse of the distance at which a ray passing through that position on the lens will intersect the principal axis. This value will be different from the power derived from the local curvature of the treatment zone, wherein such power is also a function of the distance of convergence of the rays passing through the zone along its own individual axis.

As a further example, the treatment zones 1504, 1506 may be configured as a treatment zone for treating, preventing, or slowing myopia progression. The treatment zones 1504, 1506 may be configured to have a surface shape that produces a focal ring, with the locus of each of the infinite focal points on the ring being displaced ('non-coaxial') from the geometric axis of the center zone 1502. Additional treatment zones 1504 may be used. The at least one of the treatment zones 1504, 1506 may have an annular configuration sharing a common geometric axis with the center zone 1502, and wherein the at least one of the treatment zones 1504, 1506 exhibits (that is, results in) a focal ring, with the locus of each of the infinite focal points on the ring being displaced ('non-coaxial') from the geometric axis of the center zone 1502. The at least one treatment zone 1504 may have a surface shape comprising a portion of a toroidal shape, wherein the at least one of the treatment zones 1504, 1506 is arranged as to form a continuous surface with the center zone. As an example, the portion of the toroidal shape may be derived from a torus (e.g., spheroidal torus), wherein a slice through the surface of the spheroidal torus to generate the portion of the toroidal shape comprises a right circular conical surface with the principal axis of the cone coincident with the axis of rotation about which the torus is generated.

FIG. 15B illustrates a conventional power profile of an example ophthalmic device, the power profile showing optical power vs. radial distance from the center of ophthalmic device. As shown, a center zone 1512 or region disposed at and/or adjacent to the center of the ophthalmic lens has an ADD power that has a focal point along the principal axis of the lens (coaxial) and is the first treatment zone in this example ophthalmic device. The surface of the ophthalmic lens then exhibits a generally flat optical power profile at a radius outside of the center zone 1512, which would again represent an example for an emmetropic eye, but it is readily appreciable that the entire power profile here may be adjusted to correct myopic refractive error. A second treatment zone 1514 is illustrated at about 1.40 mm to 2.00 mm, where the optical power rises from the surrounding regions and exhibits a more positive optical power. A third treatment zone 1516 is illustrated at about 3.30 mm to 4.00 mm, where the optical power rises from the surrounding regions and exhibits a more positive optical power. The conventional power profile derives the power for a given radial distance from the center of the lens from the inverse of the distance at which a ray passing through that position on the lens will intersect the principal axis. This value will be different from the power derived from the local curvature of the treatment zone, wherein such power is also a function of the distance of convergence of the rays passing through the zone along its own individual axis.

As a further example, the treatment zones 1514, 1516 may be configured as a treatment zone for treating, preventing, or slowing myopia progression. The treatment zones 1514, 1516 may be configured to have a surface shape that produces a focal ring, with the locus of each of the infinite focal points on the ring being displaced ('non-coaxial') from the geometric axis of the center zone 1512. Additional treatment zones 1514 may be used. The at least one of the treatment zones 1514, 1516 may have an annular configuration sharing a common geometric axis with the center zone 1512, and wherein the at least one of the treatment zones 1514, 1516 exhibits a focal ring, with the locus of each of the infinite focal points on the ring being displaced ('non-coaxial') from the geometric axis of the center zone 1512. The at least one treatment zone 1514 may have a surface shape comprising portion of a toroidal shape, wherein the at least one of the treatment zones 1514, 1516 is arranged as to form a continuous surface with the center zone. As an example, the portion of the toroidal shape may be derived from a torus (e.g., spheroidal torus), wherein a slice through the surface of the spheroidal torus to generate the portion of the toroidal shape comprises a right circular conical surface with the principal axis of the cone coincident with the axis of rotation about which the torus is generated.

Figure 16A:
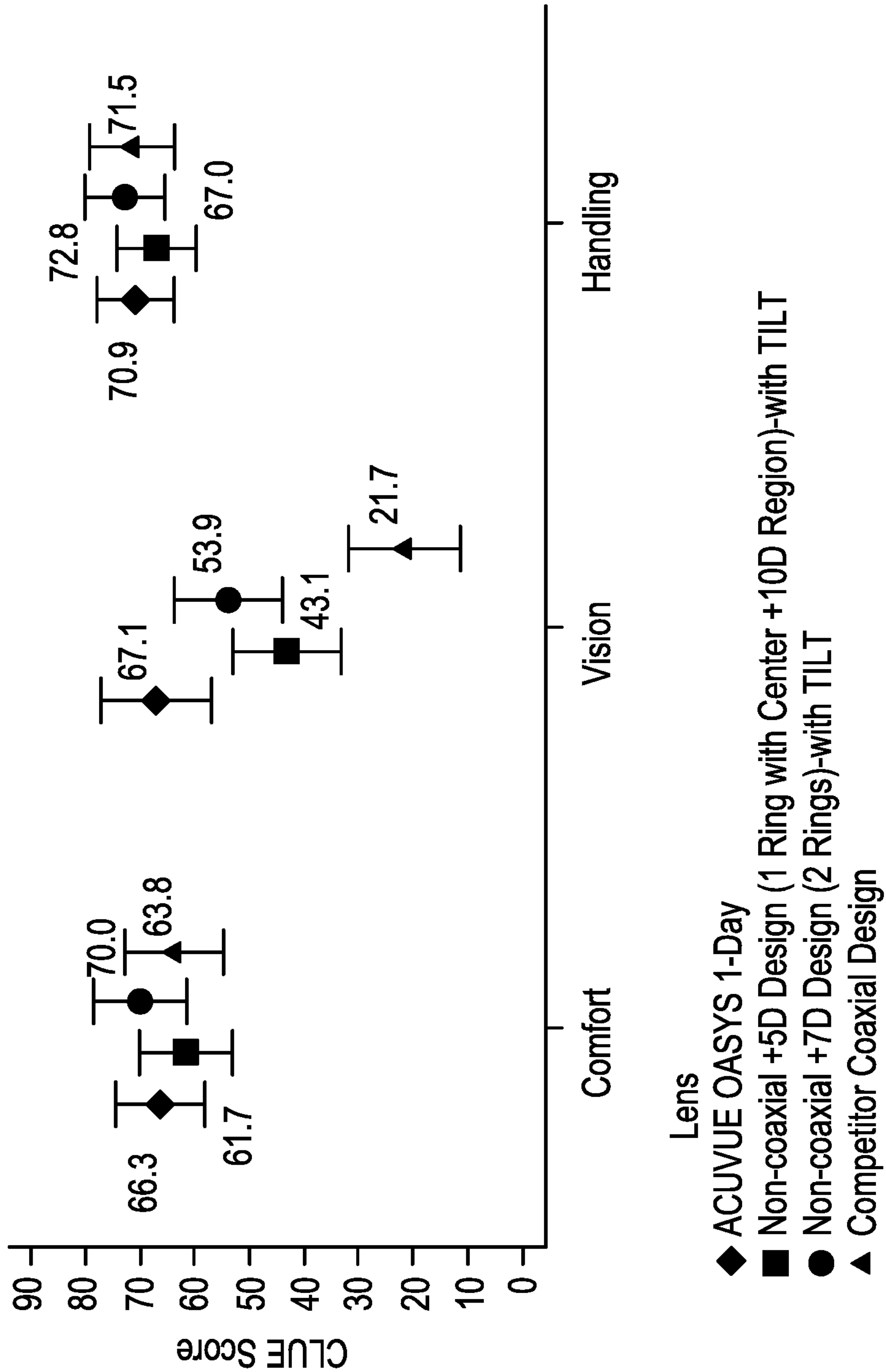
FIGS. 16A-16B illustrate comparison plots of subjective responses (as measured in Contact Lens User Experience, CLUE™ scores) after 1-3 days of lens dispensing among three multizone test lenses and one control lens (marketed, single-vision soft contact lens) regarding comfort, vision and handling, respectively, where
Figure 16B:
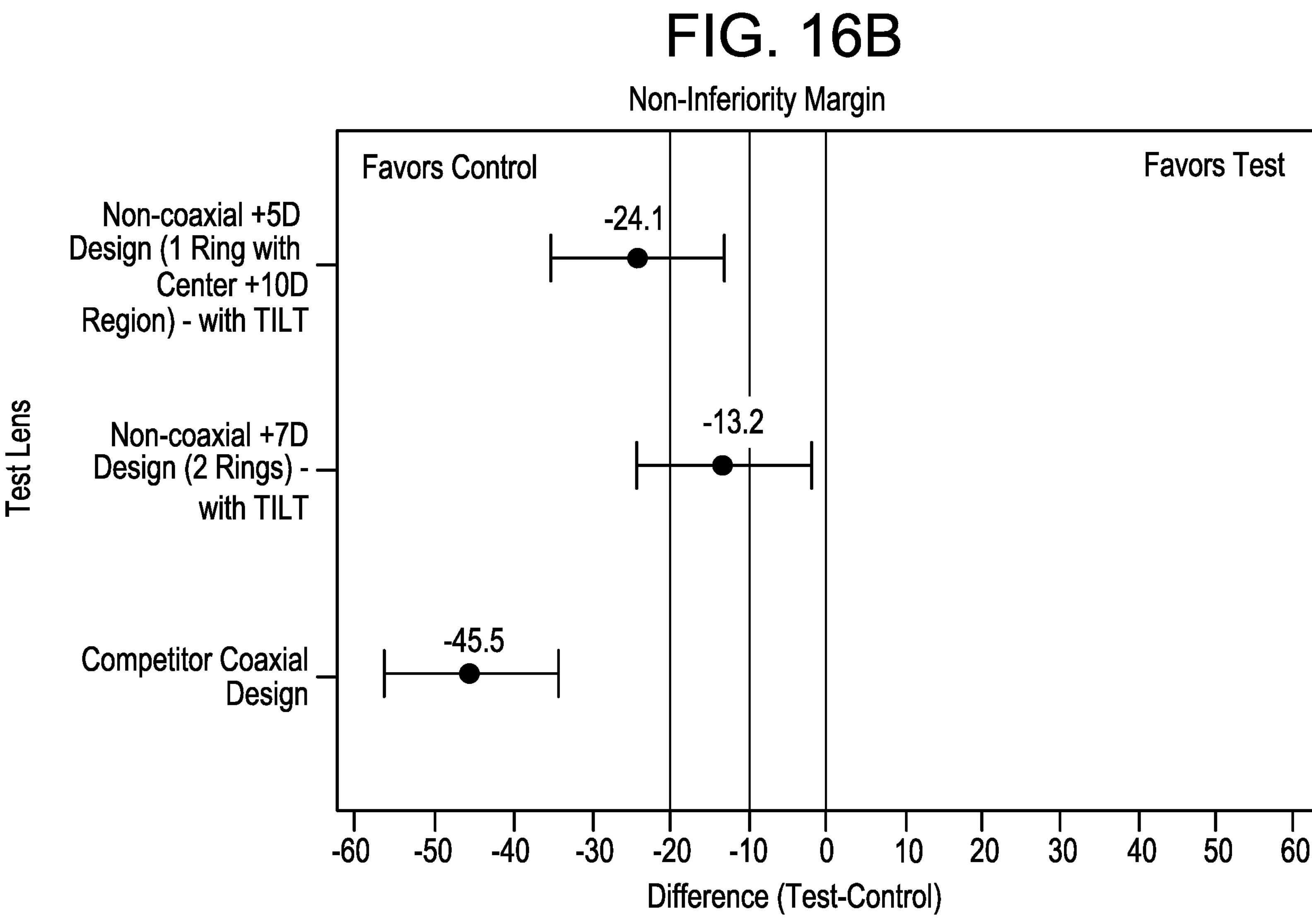

FIGS. 16A-16B illustrate comparisons of subjective responses after 1-3 days of lens dispensing among three multizone test lenses and one marketed, single-vision soft control lens. The test lenses included two novel designs as described in this disclosure and a competitor design with conventional optics incorporating concentric treatment rings, coaxial focus and an optical ADD power of between +2.00 and +2.50 D. CLUE™ scores were obtained for comfort, vision and handling. CLUE™ is a validated patient reported outcomes (PRO) questionnaire to assess patient-experience attributes of soft contact lenses in a contact-lens wearing population in the US, ages 18-65 (Wirth R J et al. Development of the Contact Lens User Experience: CLUE Scales. Optom Vis Sci. 2016; 93(8):801-808). As illustrated, a higher CLUE score is desirable. FIG. 16A shows the least squares means (LSM) and 95% confidence intervals (CI) of CLUE scores by lens type and FIG. 16B shows LSM differences and 95% CI of CLUE Vision score between each of the three test lenses and the control lens. CLUE Vision scores were significantly lower in all three multifocal test lenses than the single-vision control lens. However, the competitor lens with coaxial design had the worst vision degradation (CLUE score decreased by 45.5) compared to the two non-coaxial lens designs (by 24.1 and 13.2, respectively).

Figure 17A:
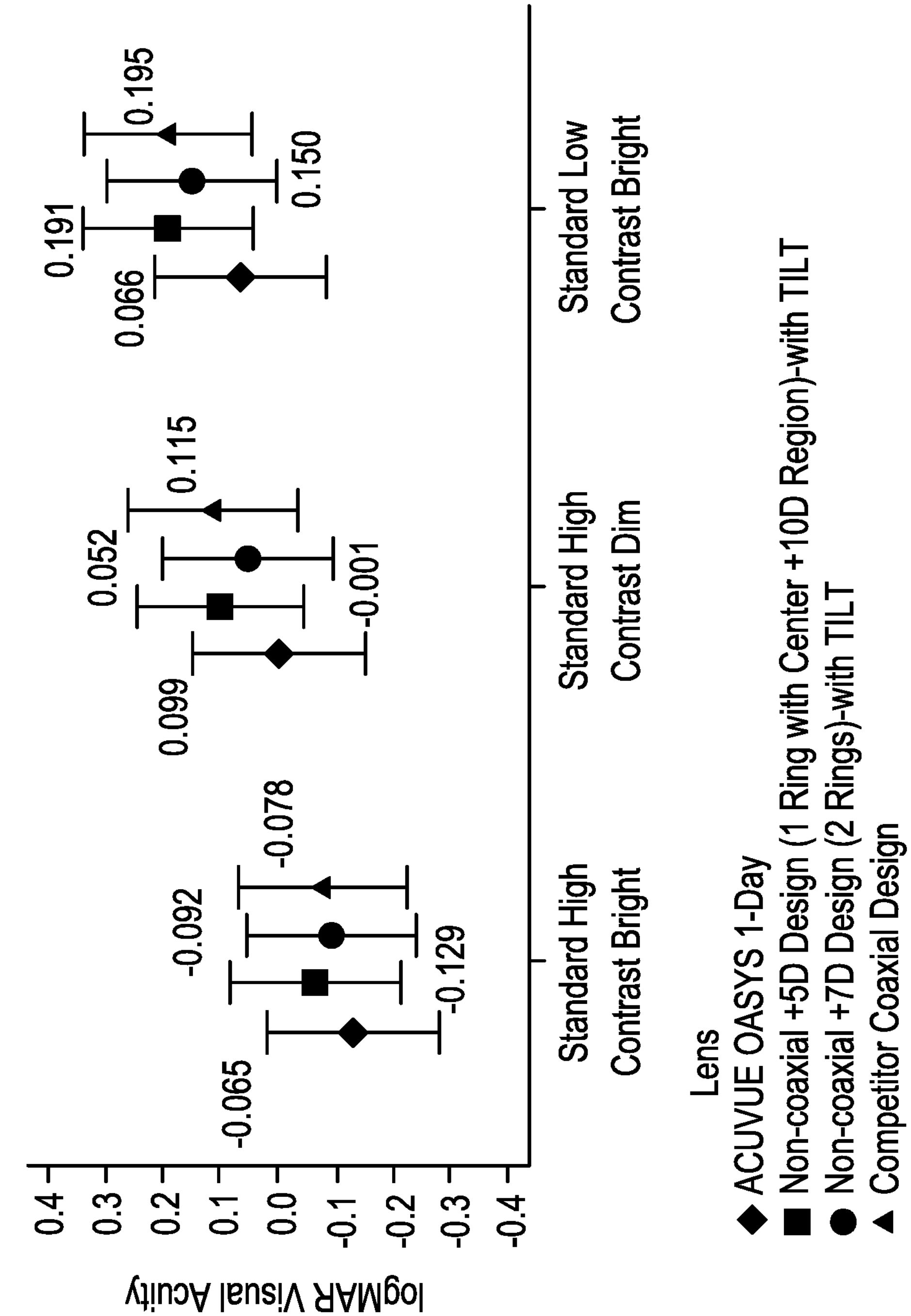
FIGS. 17A-17B illustrate comparison plots of monocular (A) and binocular (B) log MAR visual acuity among three multizone test lenses and one control lens (marketed, single-vision soft contact lens) under three different contrast/lighting conditions (LSM and 95% CI).
Figure 17B:
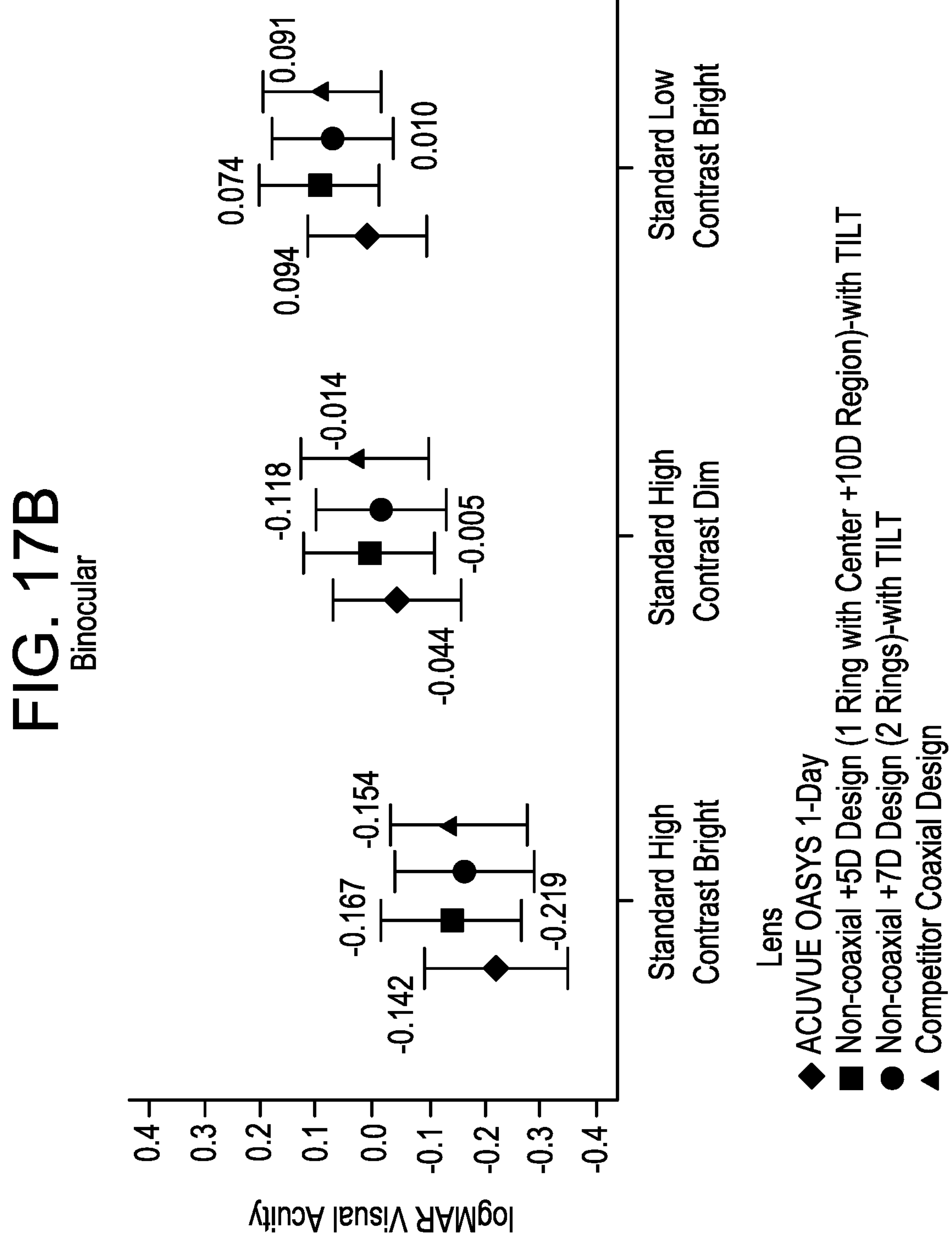

FIGS. 17A-17B illustrate comparison plots of monocular (A) and binocular (B) log MAR visual acuity among three multizone test lenses and one control lens (marketed, single-vision soft contact lens) under three different contrast/lighting conditions (LSM and 95% CI). It is important to note that the competitor coaxial design had an optical ADD power of between +2.00 and +2.50 D.

Figure 18A:
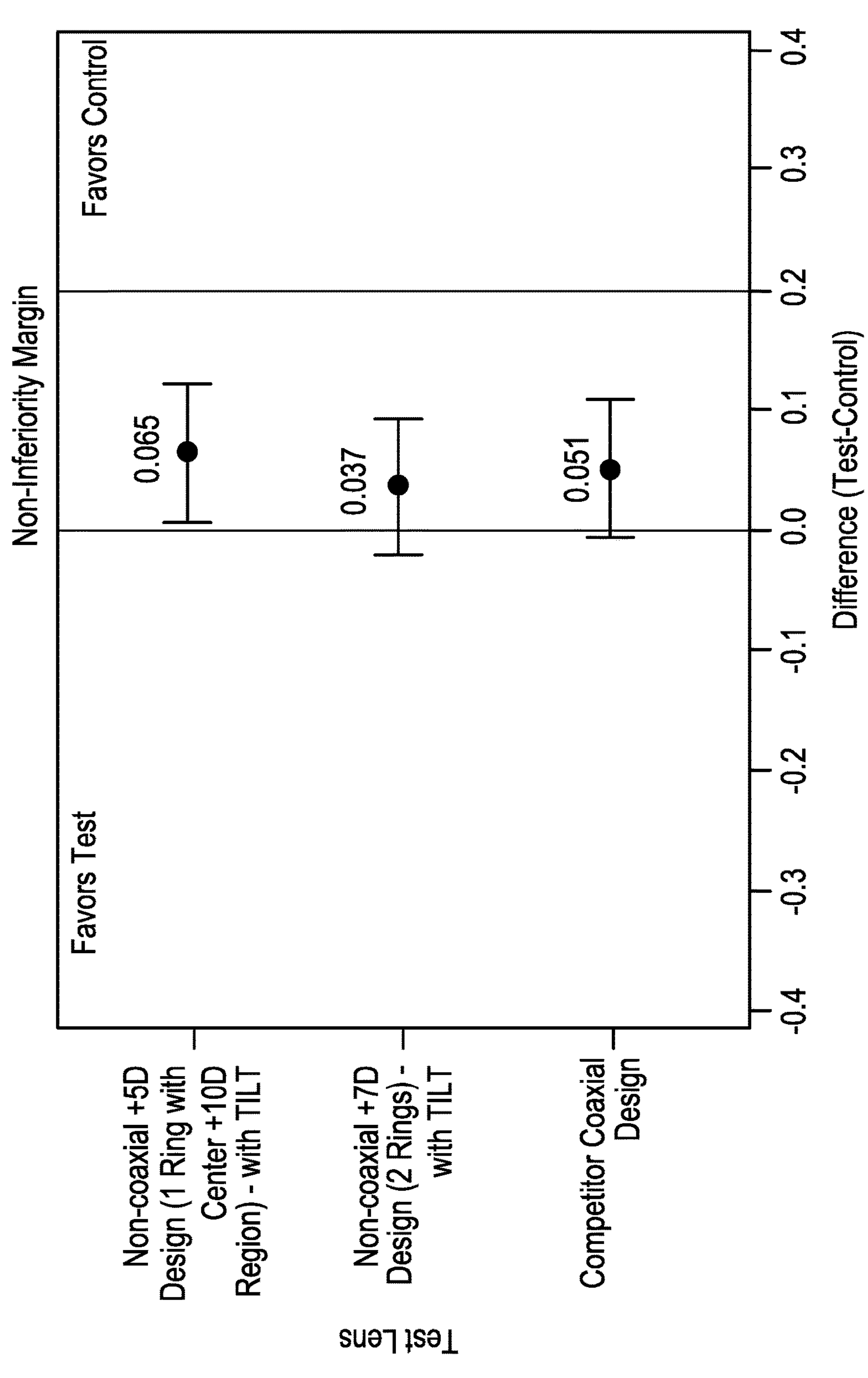
FIGS. 18A-18B illustrate comparison plots of a difference in monocular (A) and binocular (B) log MAR visual acuity between each of the three test lenses and the control lens under High Contrast Bright conditions (LSM Difference and 95% CI).
Figure 18B:
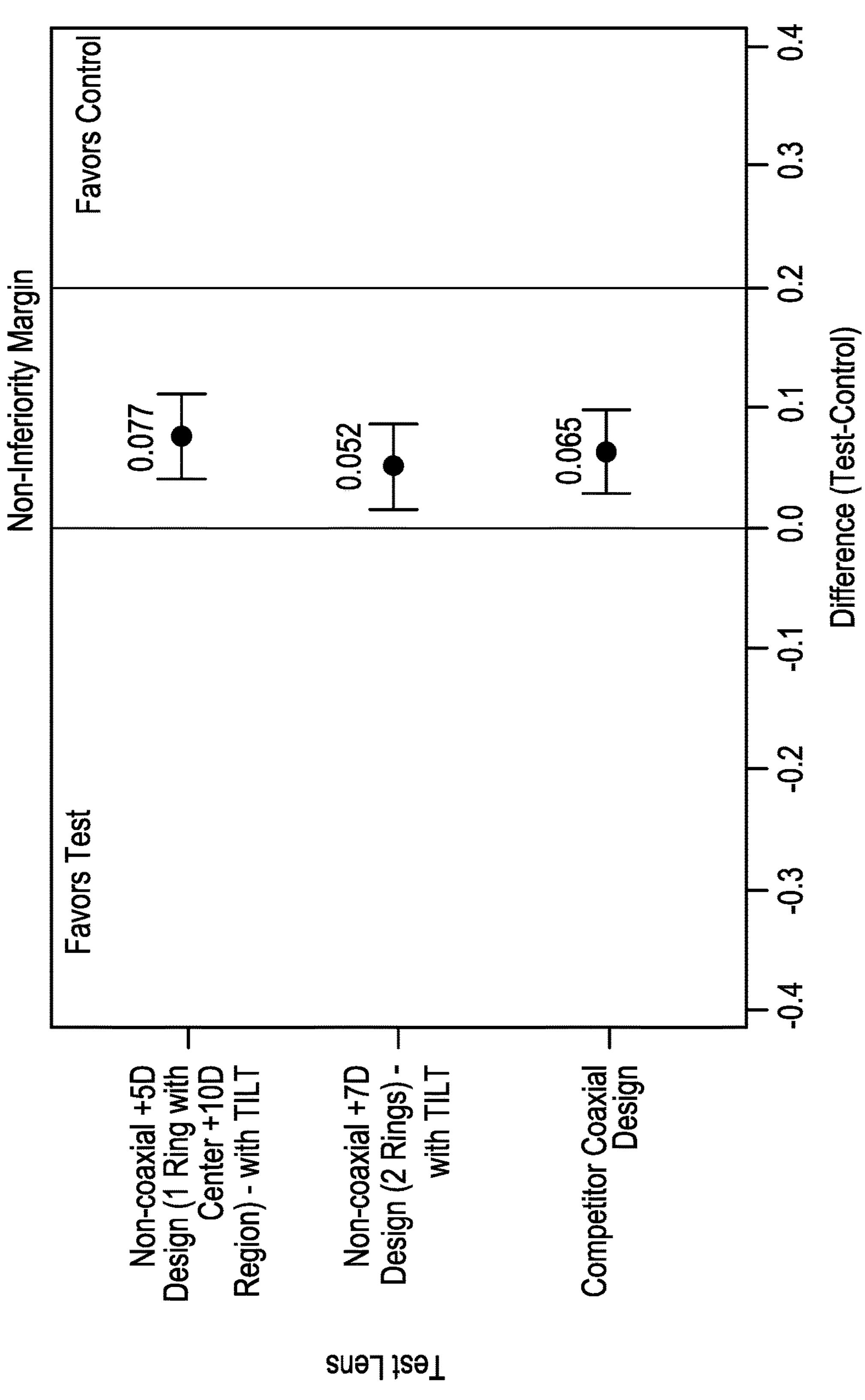

FIGS. 18A-18B illustrate comparison plots of a difference in monocular (A) and binocular (B) log MAR visual acuity between each of the three test lenses and the control lens under High Contrast Bright conditions (LSM Difference and 95% CI). All three test lenses had better than 20/20 (0.00 log MAR) visual acuity (both monocular and binocular). Monocular log MAR visual acuity was, on average, 0.07, 0.04 and 0.05 log MAR worse than the control lens for non-coaxial +5 D, non-coaxial +7 D and competitor coaxial designs, respectively, which were about half to one line worse. Binocular log MAR visual acuity was, on average, 0.08, 0.05 and 0.07 log MAR worse than the control lens for non-coaxial +5 D, non-coaxial +7 D and competitor coaxial designs, respectively, which were about half to one line worse than the control lens.

Figure 19A:
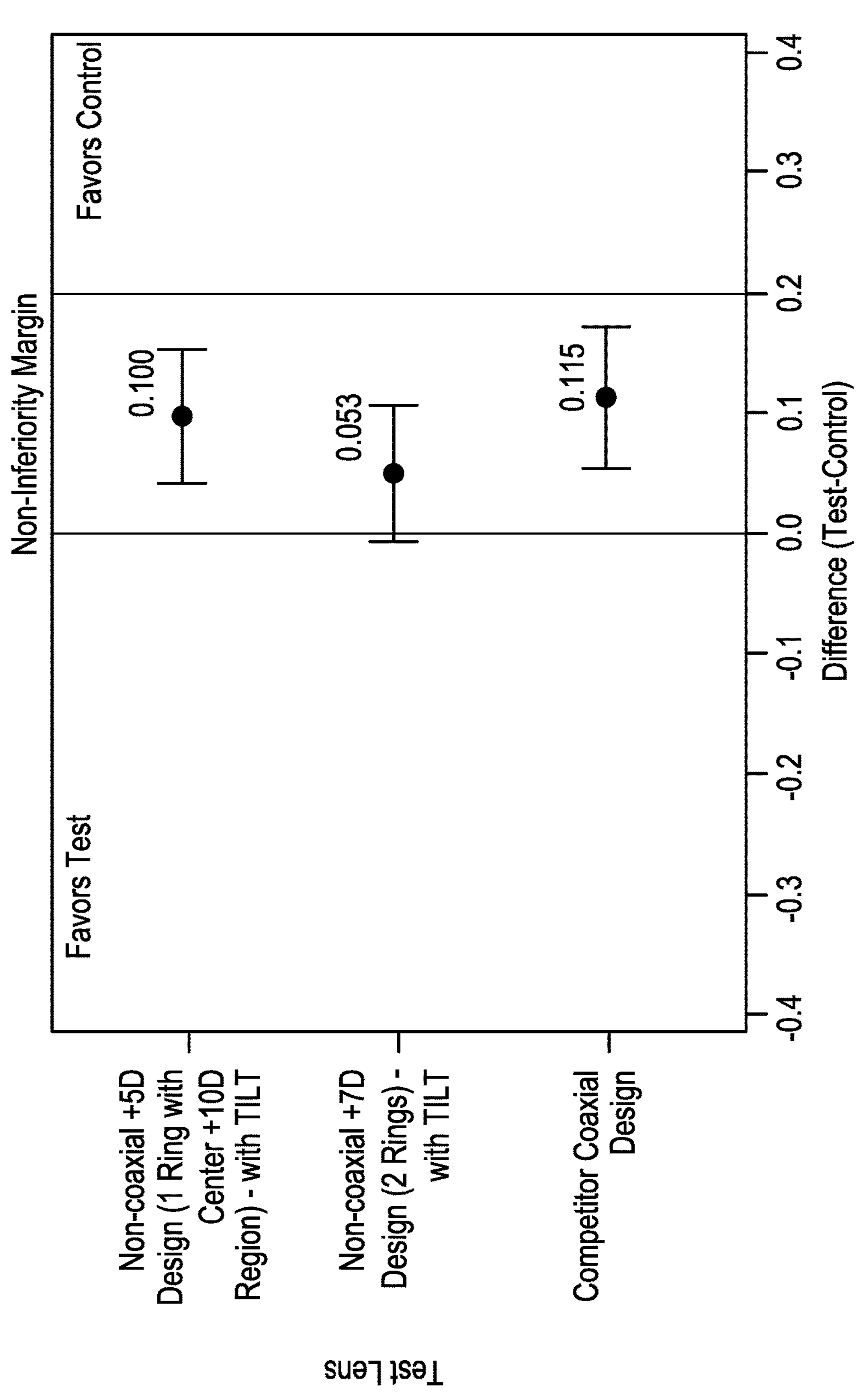
FIGS. 19A-19B illustrate comparison plots of a difference in monocular (A) and binocular (B) log MAR visual acuity between each of the three test lenses and the control lens under High Contrast Dim conditions (LSM Difference and 95% CI).
Figure 19B:
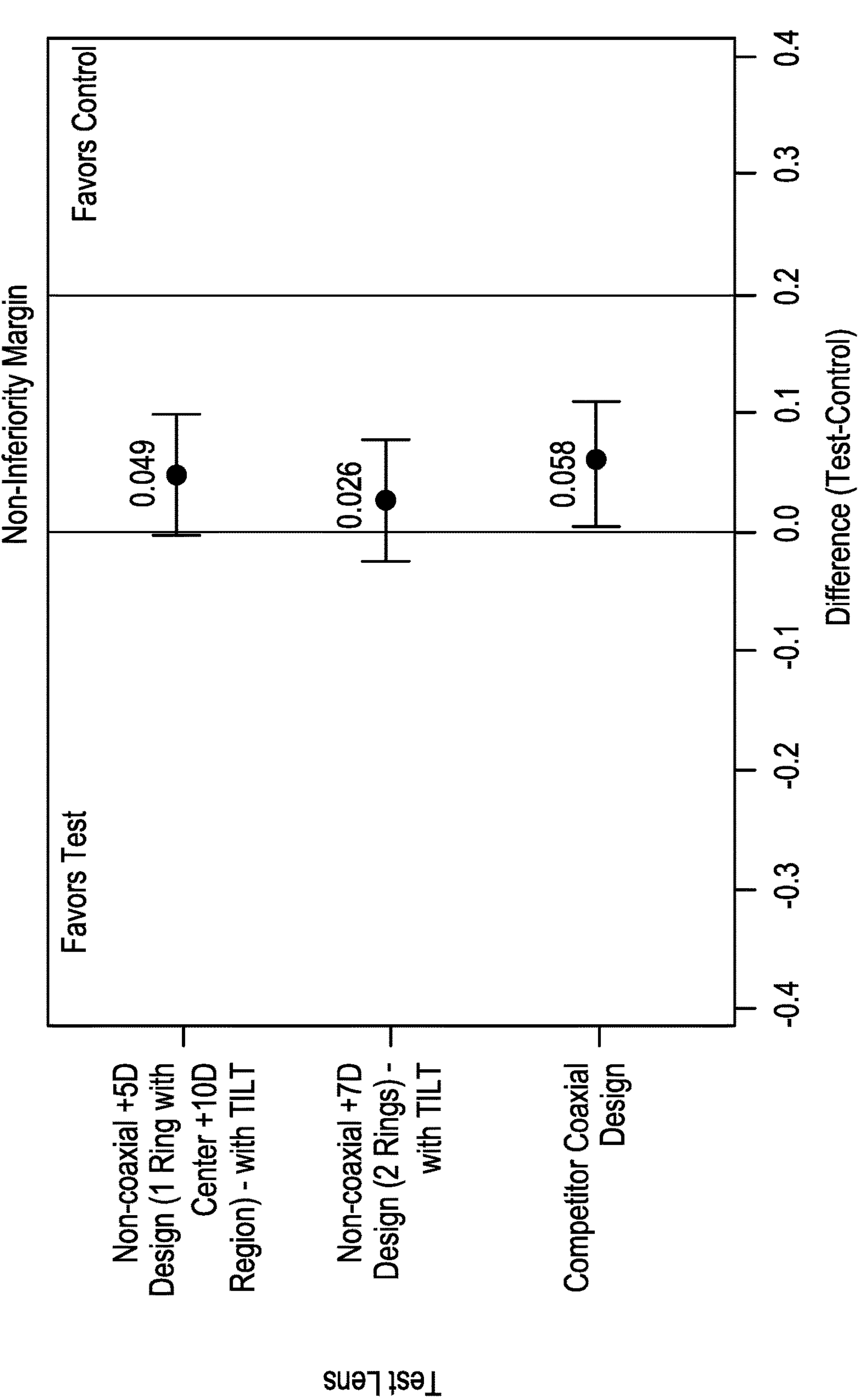

FIGS. 19A-19B illustrate comparison plots of a difference in monocular (A) and binocular (B) log MAR visual acuity between each of the three test lenses and the control lens under High Contrast Dim conditions (LSM Difference and 95% CI). Monocular log MAR visual acuity was, on average, 0.10, 0.05 and 0.12 log MAR worse than the control lens for non-coaxial +5 D, non-coaxial +7 D and competitor coaxial designs, respectively, which were about half to one line worse than the control lens. Binocular log MAR visual acuity was, on average, 0.05, 0.03 and 0.06 log MAR worse than the control lens for non-coaxial +5 D, non-coaxial +7 D and competitor coaxial designs, respectively, which were about half a line worse than the control lens.

Figure 20A:
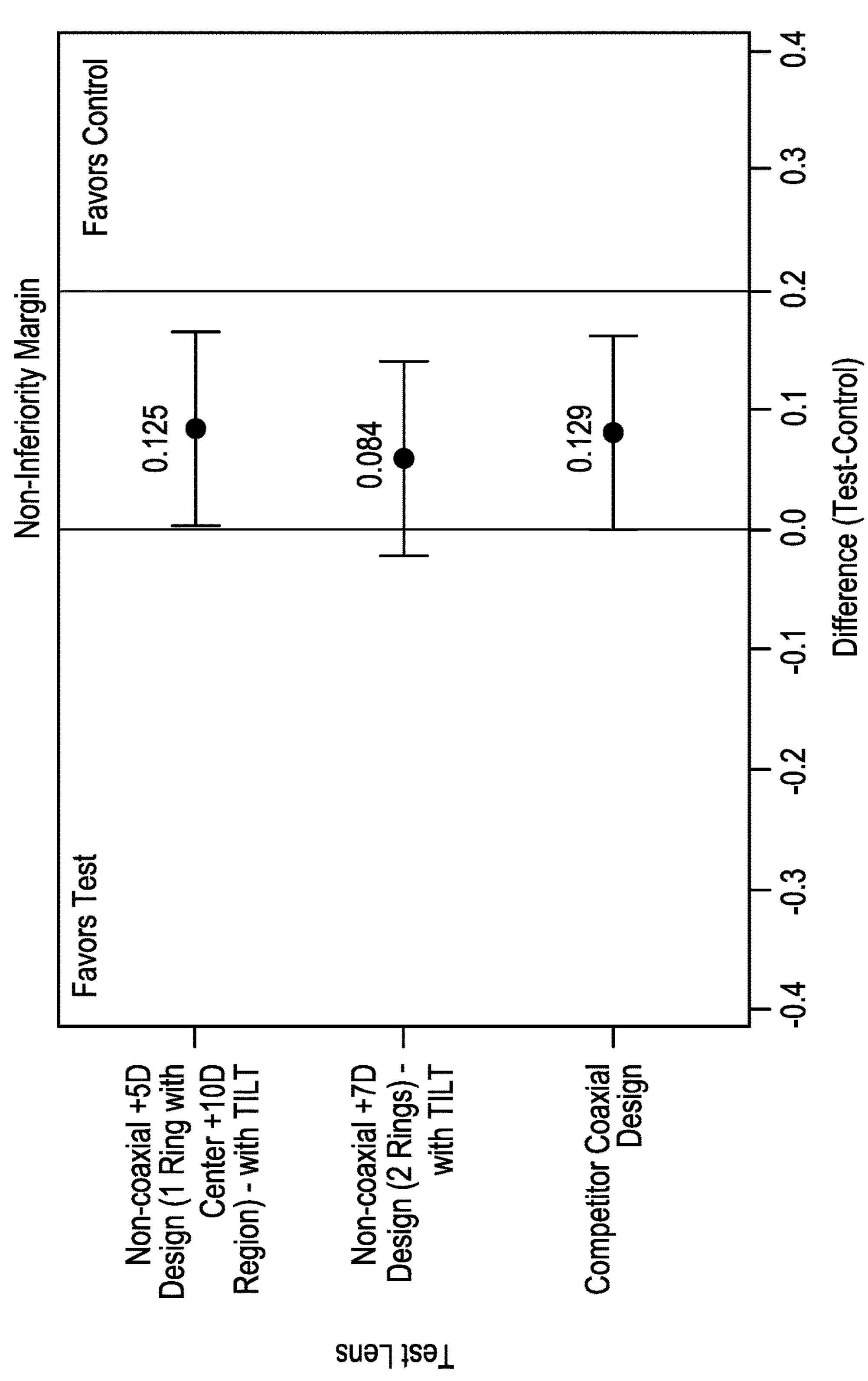
FIGS. 20A-20B illustrate comparison plots of a difference in monocular (A) and binocular (B) log MAR visual acuity between each of the three test lenses and the control lens under Low Contrast Bright conditions (LSM Difference and 95% CI).
Figure 20B:
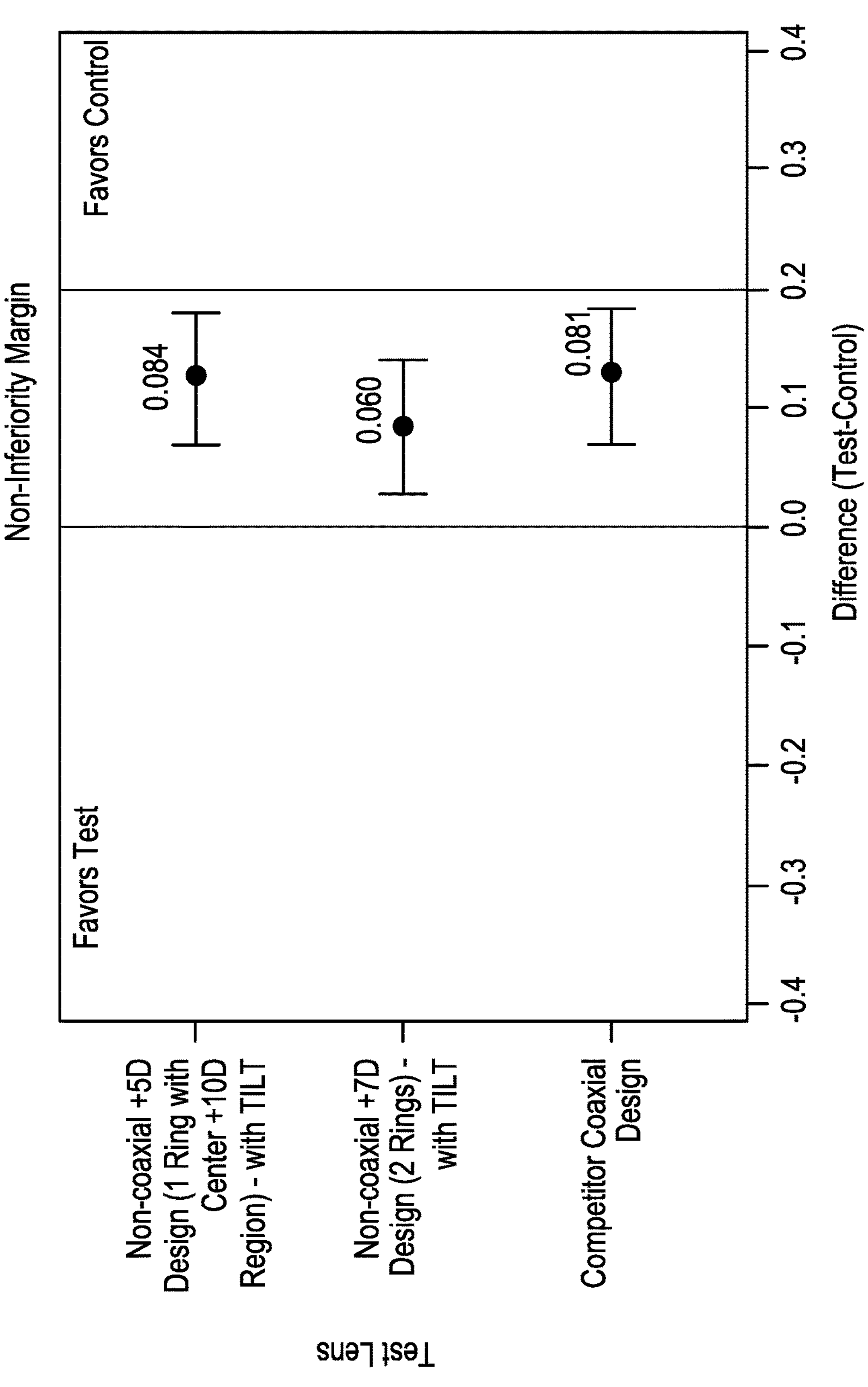

FIGS. 20A-20B illustrate comparison plots of a difference in monocular (A) and binocular (B) log MAR visual acuity between each of the three test lenses and the control lens under Low Contrast Bright conditions (LSM Difference and 95% CI). It is important to note that the competitor coaxial design had an optical ADD power of between +2.00 and +2.50 D. Monocular log MAR visual acuity was, on average, 0.13, and 0.13 log MAR worse than the control lens for non-coaxial +5 D, non-coaxial +7 D and competitor coaxial designs, respectively, which were about one to one and a half lines worse than the control. Binocular log MAR visual acuity was, on average, 0.08, and 0.08 log MAR worse than the control lens for non-coaxial +5 D, non-coaxial +7 D and competitor coaxial designs, respectively, which were about half to one line worse than the control lens.

The non-coaxial +7 D design exhibited the least degradation in CLUE™ score and log MAR visual acuity (both monocular and binocular under all three contrast/lighting conditions) among the three test lenses compared to the control lens. Visual acuity was similar between the non-coaxial +5 D and the competitor coaxial designs but the CLUE™ score for the competitor lens was worse. Note that the competitor design with conventional coaxial optics had an optical ADD power of only between +2.00 and +2.50 D.

These results demonstrate the advantage of the current invention. Previous myopia control designs with conventional optics are limited in myopia control efficacy by the extent to which they degrade vision. Exemplary embodiments of the current invention can be more effective at slowing myopia progression but with less impact on vision.

Currently available contact lenses remain a cost-effective means for vision correction. The thin plastic lenses fit over the cornea of the eye to correct vision defects, including myopia or nearsightedness, hyperopia or farsightedness, astigmatism, and presbyopia, i.e., the loss of the ability of the crystalline lens to accommodate. Contact lenses are available in a variety of forms and are made of a variety of materials to provide different functionality.

Daily wear soft contact lenses are typically made from soft polymer materials combined with water for oxygen permeability. Daily wear soft contact lenses may be daily disposable or extended wear disposable. Daily disposable contact lenses are usually worn for a single day and then thrown away, while extended wear or frequent replacement disposable contact lenses are usually worn for a period of up to thirty days. Colored soft contact lenses use different materials to provide different functionality. For example, a visibility tint contact lens uses a light tint to aid the wearer in locating a dropped contact lens, enhancement tint contact lenses have a translucent tint that is meant to enhance one's natural eye color, the color tint contact lens comprises a darker, opaque tint meant to change one's eye color, and the light filtering tint contact lens functions to enhance certain colors while muting others. Rigid gas permeable hard contact lenses are made from siloxane-containing polymers but are more rigid than soft contact lenses and thus hold their shape and are more durable. Bifocal contact lenses are designed specifically for patients with presbyopia and are available in both soft and rigid varieties. Toric contact lenses are designed specifically for patients with astigmatism and are also available in both soft and rigid varieties. Combination lenses combining different aspects of the above are also available, for example, hybrid contact lenses.

It is important to note that the lens designs of the present disclosure may be incorporated into any number of different contact lenses formed from any number of materials. Specifically, the lens design of the present disclosure may be utilized in any of the contact lenses described herein, including, daily wear soft contact lenses, rigid gas permeable contact lenses, bifocal contact lenses, toric contact lenses and hybrid contact lenses. In addition, although the disclosure is described with respect to contact lenses, it is important to note that the concept of the present disclosure may be utilized in spectacle lenses, intraocular lenses, corneal inlays and onlays.

Although shown and described in what is believed to be the most practical and preferred embodiments, it is apparent that departures from specific designs and methods described and shown will suggest themselves to those skilled in the art and may be used without departing from the spirit and scope of the disclosure. The present disclosure is not restricted to the particular constructions described and illustrated, but should be constructed to cohere with all modifications that may fall within the scope of the appended claims. Moreover, the recitation of the term comprising may include consisting essentially of and/or consisting of such that support is found herein for such terms by the use of the term comprising.

What is claimed is:

1. An ophthalmic lens for at least one of slowing, retarding or preventing myopia progression, the ophthalmic lens comprising:

a center zone with a negative power for myopic vision correction, the center zone having a principal axis orthogonal to a surface thereof and passing through a center of the ophthalmic lens; and at least one treatment zone surrounding the center zone, the at least one treatment zone having a power profile comprising a positive power relative to the center zone, the at least one treatment zone having a surface shape projecting outwardly from a front surface of said ophthalmic lens and comprising a portion of a generally toroidal shape, wherein the at least one treatment zone is arranged as to form a continuous surface with the center zone, and wherein the at least one treatment zone has a tilt angle between +0.035 and +0.3215 degrees relative to a zero-angle comparator, wherein the tilt angle is designated as zero when a central ray passing through a mid-annulus of the treatment zone passes through an intersection point of a retinal plane of a wearer of the ophthalmic lens and the principal axis, wherein a positive tilt angle causes the central ray passing through the mid-annulus of the treatment zone to intersect the principal axis anterior to the retinal plane, and wherein the at least one treatment zone has an annular configuration sharing the principal axis with the center zone.

2. The ophthalmic lens according to claim 1, wherein the tilt angle is configured to direct the central ray passing through the mid-annulus of the treatment zone to cross the principal axis at a point between the retinal plane and a point on the principal axis that represents a coincident point focus of the treatment zone.

3. The ophthalmic lens of claim 1, wherein the portion of the generally toroidal shape may be derived from a torus (e.g., a spheroidal torus), after making a slice in the shape of the surface of a right circular cone through the surface of the spheroidal torus wherein the principal axis of the cone is coincident with the axis of rotation about which the torus is generated.

4. The ophthalmic lens according to claim 1, further comprising a transition zone disposed between then center zone and the at least one treatment zone such that the at least one treatment zone, the transition zone, and the center zone form a continuous surface.

5. The ophthalmic lens according to claim 1, wherein the at least one treatment zone comprises an ADD power relative to myopia correction power of greater than +5.00 D.

6. The ophthalmic lens according to claim 1, wherein the at least one treatment zone comprises an optical power from about −10.00 D to about +15.00 D.

7. The ophthalmic lens according to claim 6, wherein the tilt angle is dependent upon the optical power of the treatment zone.

8. The ophthalmic lens according to claim 1, wherein a diameter of the center zone is about 3 mm to about 7 mm.

9. The ophthalmic lens according to claim 1, wherein the at least one treatment zone has an outer margin at about 4.5 mm from a center of the lens.

10. The ophthalmic lens according to claim 1, wherein a halo effect is minimized.

11. The ophthalmic lens according to claim 1, wherein the ophthalmic lenses comprises a contact lens.

12. The ophthalmic lens according to claim 1, wherein the ophthalmic lenses comprises a spectacle lens.

13. The ophthalmic lens according to claim 1, wherein the ophthalmic lens comprises an intraocular lens, a corneal inlay, or a corneal onlay.

14. The ophthalmic according to claim 1, further comprising one or more stabilization mechanisms.

15. The ophthalmic lens according to claim 1, wherein a negative tilt angle causes the central ray passing through the mid-annulus of the treatment zone to intersect the principal axis posterior to the retinal plane.

16. An ophthalmic lens for at least one of slowing, retarding or preventing myopia progression, the ophthalmic lens comprising:

a center zone with a negative power for myopic vision correction, the center zone having a principal axis orthogonal to a surface thereof and passing through a center of the ophthalmic lens; and at least one treatment zone surrounding the center zone, the at least one treatment zone having a power profile comprising a positive power relative to the center zone, the at least one treatment zone having a surface shape projecting outwardly from a front surface of said ophthalmic lens and comprising a portion of a generally toroidal shape, wherein the at least one treatment zone is arranged as to form a continuous surface with the center zone, and wherein the at least one treatment zone has a tilt angle between +0.035 and +0.3215 degrees relative to a zero-angle comparator, wherein the tilt angle is designated as zero when a central ray passing through a mid-annulus of the treatment zone passes through an intersection point of a retinal plane of a wearer of the ophthalmic lens and the principal axis, and wherein a positive tilt angle causes the central ray passing through the mid-annulus of the treatment zone to intersect the principal axis anterior to the retinal plane, wherein the at least one treatment zone exhibits a focal ring with a locus of each of infinite focal points on the ring being displaced non-coaxially from the principal axis, and wherein the at least one treatment zone has an annular configuration sharing the principal axis with the center zone.

17. An ophthalmic lens for at least one of slowing, retarding or preventing myopia progression, the ophthalmic lens comprising:

a center zone with a negative power for myopic vision correction, the center zone having a principal axis orthogonal to a surface thereof and passing through a center of the ophthalmic lens; and at least one treatment zone surrounding the center zone, the at least one treatment zone having a power profile comprising a positive power relative to the center zone, the at least one treatment zone having a surface shape projecting outwardly from a front surface of said ophthalmic lens and comprising a portion of a generally toroidal shape, wherein the at least one treatment zone is arranged as to form a continuous surface with the center zone, and wherein the at least one treatment zone has a tilt angle between +0.035 and +0.3215 degrees relative to a zero-angle comparator, wherein the tilt angle is designated as zero when a central ray passing through a mid-annulus of the treatment zone passes through an intersection point of a retinal plane of a wearer of the ophthalmic lens and the principal axis, and wherein a positive tilt angle causes the central ray passing through the mid-annulus of the treatment zone to intersect the principal axis anterior to the retinal plane, and wherein the at least one treatment zone exhibits a focal ring with a locus of each of infinite focal points on the ring being displaced non-coaxially from the principal axis.

* * * * *